(12) United States Patent
Huber et al.

(10) Patent No.: US 10,598,534 B2
(45) Date of Patent: Mar. 24, 2020

(54) DENSITY MEASURING DEVICE

(71) Applicant: Endress + Hauser Flowtec AG, Reinach (CH)

(72) Inventors: Christof Huber, Bern (CH); Vivek Kumar, Allschwil (CH); Philipp Montsko, Rickenbach (DE); Tobias Schwer, Kirchzarten (DE)

(73) Assignee: Endress + Hauser Flowtec AG, Reinach (CH)

( * ) Notice: Subject to any disclaimer, the term of this patent is extended or adjusted under 35 U.S.C. 154(b) by 106 days.

(21) Appl. No.: 15/102,626

(22) PCT Filed: Nov. 3, 2014

(86) PCT No.: PCT/EP2014/073520
§ 371 (c)(1),
(2) Date: Jun. 8, 2016

(87) PCT Pub. No.: WO2015/086224
PCT Pub. Date: Jun. 18, 2015

(65) Prior Publication Data
US 2016/0349091 A1 Dec. 1, 2016

(30) Foreign Application Priority Data
Dec. 9, 2013 (DE) .................. 10 2013 113 689

(51) Int. Cl.
*G01F 1/84* (2006.01)
*G01N 9/00* (2006.01)
(Continued)

(52) U.S. Cl.
CPC .......... *G01F 1/8472* (2013.01); *G01F 1/8468* (2013.01); *G01N 9/002* (2013.01);
(Continued)

(58) Field of Classification Search
CPC .............................. G01F 1/8472; G01F 1/8468
(Continued)

(56) References Cited

U.S. PATENT DOCUMENTS 4,801,897 A 1/1989 Flecken
5,533,381 A 7/1996 Seale
(Continued)

FOREIGN PATENT DOCUMENTS

CN 101151516 A 3/2008
CN 101625259 A 1/2010
(Continued)

OTHER PUBLICATIONS

German Search Report, German Patent Office, Munich, DE, dated Sep. 17, 2014.
(Continued)

*Primary Examiner* — John Fitzgerald
*Assistant Examiner* — Rodney T Frank
(74) *Attorney, Agent, or Firm* — Kelly J. Smith; PatServe

(57) ABSTRACT

The density measuring device serves for measuring density, ρ, of a flowable medium and comprises a measuring device electronics (ME) as well as a measuring transducer (MT) electrically connected therewith. The measuring transducer includes a measuring tube (10), an oscillation exciter (41) for exciting and maintaining oscillations and an oscillation sensor (51) for registering oscillations of the at least one measuring tube. The measuring device electronics is adapted by means of an oscillation measurement signal ($s_1$) as well as an exciter signal ($e_1$) to adjust a drive force effecting wanted oscillations (namely oscillations with a predetermined wanted frequency, $f_N$) of the measuring tube. The drive force is adjusted in such a manner that during a predetermined phase control interval a phase shift angle, $\varphi_N$, by which a velocity response, $V_N$, of the measuring tube Is
(Continued)

phase shifted relative to a wanted force component, $F_N$, of the drive force, is less than −20° and greater than −80°, and/or the wanted frequency has a frequency value, which corresponds to greater than 1.00001 times, equally as well less than 1.001 times, a frequency value of an instantaneous resonant frequency of the measuring tube. Moreover, the measuring device electronics is adapted based on the oscillation measurement signal ($s_1$) present during the phase control interval to ascertain at least one frequency measured value, $X_f$, which represents the wanted frequency for the phase control interval, as well as also with application of the frequency measured value, $X_f$, to generate a density measured value, $X_\rho$, representing a density, $\rho$.

28 Claims, 10 Drawing Sheets

(51) Int. Cl.
*G01N 11/16* (2006.01)
*G01N 11/02* (2006.01)

(52) U.S. Cl.
CPC ............ *G01N 11/02* (2013.01); *G01N 11/16* (2013.01); *G01N 2009/006* (2013.01)

(58) Field of Classification Search
USPC ........................................................ 73/30.03
See application file for complete search history.

(56) References Cited

U.S. PATENT DOCUMENTS

| | | |
|---|---|---|
| 5,648,616 A | 7/1997 | Keel |
| 7,974,792 B2 | 7/2011 | Duffill |
| 8,396,674 B2 | 3/2013 | Gebhardt |
| 8,763,443 B2 | 7/2014 | Hussain |
| 2010/0257943 A1* | 10/2010 | Huber ................ G01F 1/74 |
| | | 73/861.357 |
| 2012/0123705 A1 | 5/2012 | Drahm |
| 2013/0291652 A1* | 11/2013 | Rieder ............. G01F 1/8404 |
| | | 73/861.357 |

FOREIGN PATENT DOCUMENTS

| | | |
|---|---|---|
| CN | 102639973 A | 8/2012 |
| CN | 102686986 A | 9/2012 |
| DE | 8712331 U1 | 1/1988 |
| DE | 102008046891 A1 | 1/2010 |
| DE | 102010044179 A1 | 5/2012 |
| WO | 2006104690 A1 | 10/2006 |
| WO | 2009056270 A2 | 5/2009 |

OTHER PUBLICATIONS

International Search Report, EPO, The Netherlands, dated Jan. 12, 2015.
English Translation of the International Preliminary Report on Patentability, WIPO, Geneva, CH, dated Jun. 23, 2016.

* cited by examiner

DENSITY MEASURING DEVICE

TECHNICAL FIELD

The invention relates to a vibronic density measuring device for measuring density, ρ, of a flowable medium, especially a fluid flowing in a pipeline.

BACKGROUND DISCUSSION

Often applied in industrial measurements technology, especially also in connection with the control and monitoring of automated manufacturing processes, for highly accurate ascertaining of densities of media, for example, liquids or gases, flowing in a process line, for example, a pipeline, are vibronic density measuring devices formed by means of a measuring device electronics (most often at least one microprocessor) as well as a measuring transducer of vibration-type electrically connected with the measuring device electronics and flowed-through during operation by the medium to be measured. Such density measuring devices—embodied, for example, as so-called four-conductor- or also as so-called two conductor devices—have been known for a long time, not least of all also in the form of Coriolis mass flow-/density measuring devices or also in the form of viscosity-density measuring devices, and are established in industrial applications. Examples of such vibronic density measuring devices, respectively suitable measuring transducers, are described, among other things, in US-A 2004/0123645, US-A 2006/0096390, US-A 2007/0119264, US-A 2008/0047362, US-A 2008/0190195, US-A 2010/0005887, US-A 2010/0011882, US-A 2010/0257943, US-A 2011/0161017, US-A 2011/0219872, US-A 2011/0265580, US-A 2012/0123705, U.S. Pat. Nos. 4,491,009, 4,524,610, 4,801,897, 4,996,871, 5,024,104, 5,287,754, 5,291,792, 5,349,872, 5,531,126, 5,705,754, 5,796,010, 5,796,011, 5,831,178, 5,945,609, 5,965,824, 6,006,609, 6,092,429, 6,223,605, 6,311,136, 6,477,901, 6,513,393, 6,647,778, 6,666,098, 6,651,513, 6,711,958, 6,840,109, 6,920,798, 7,017,424, 7,059,176, 7,077,014, 7,200,503, 7,216,549, 7,325,462, 7,360,451, 7,792,646, Published International Applications, WO-A 00/34748, WO-A 01/02 816, WO-A 2008/059262, WO-A 2013/092104, WO-A 85/05677, WO-A 88/02853, WO-A 89/00679, WO-A 94/21999, WO-A 95/03528, the WO-A 95/16897, WO-A 95/29385, WO-A 98/02725, WO-A 99/40 394, WO-A 00/34748 or also in the not earlier published German patent applications DE102013101369.4, DE102013102708.3, respectively DE102013102711.3. The measuring transducer of each of the density measuring devices shown therein comprises at least one, at least sectionally straight and/or at least sectionally curved, e.g. U-, V-, S-, Z- or -shaped, measuring tube having a lumen surrounded by a tube wall and serving for guiding the medium, wherein the tube wall, depending on application, is typically made of a metal, for instance, titanium, respectively a titanium alloy, tantalum, respectively a tantalum alloy, zirconium, respectively a zirconium alloy, a stainless steel or a nickel based alloy, or, for example, also of silicon. A caliber of the measuring tube can lie, depending on application, typically in a range between 0.5 mm and 100 mm.

The at least one measuring tube of such a measuring transducer is adapted to guide medium in the lumen and during that to be caused to vibrate such that the at least one measuring tube executes wanted oscillations, namely mechanical oscillations about a resting position with a wanted frequency co-determined by the density of the medium and consequently usable as a measure for the density. In the case of conventional density measuring devices, typically bending oscillations at a natural resonant frequency serve as wanted oscillations, for example, such bending oscillations, which correspond to a natural bending oscillation, fundamental mode inherent to the measuring transducer. In such case, the oscillations of the measuring tube are resonant oscillations, which have exactly one oscillatory antinode. The wanted oscillations are in the case of an at least sectionally curved measuring tube additionally typically so embodied that the measuring tube moves in a pendulum-like manner about an imaginary oscillation axis imaginarily connecting an inlet-side end and an outlet-side end of the measuring tube in the manner of a cantilever clamped on one end, while, in contrast, in the case of measuring transducers with a straight measuring tube the wanted oscillations are most often bending oscillations in a single imaginary plane of oscillation. It is additionally known, at times, to excite the at least one measuring tube even to lasting oscillations outside of resonance for the purpose of performing repeated checks of the measuring transducer during operation of the density measuring device, as well as to evaluate the oscillations outside of resonance, for example, in order, such as described in the aforementioned US-A 2012/0123705, to detect possible damage to the at least one measuring tube as early as possible, damage which can bring about an undesired lessening of the accuracy of measurement and/or the operational safety of the respective density measuring device.

In the case of measuring transducers with two measuring tubes, these are most often connected into the particular process line via a distributor piece extending on the inlet side between the measuring tubes and an inlet-side connecting flange as well as via a distributor piece extending on the outlet side between the measuring tubes and an outlet-side connecting flange. In the case of measuring transducers with a single measuring tube, such communicates with the process line most often via a connecting tube opening on the inlet side as well as via a connecting tube opening on the outlet side. Furthermore, measuring transducers with a single measuring tube comprise, in each case, at least one one piece or multipart, for example, tube-, box- or plate-shaped, counteroscillator, which is coupled to the measuring tube at a first coupling zone on the inlet side and is coupled to the measuring tube at a second coupling zone on the outlet side, and which during operation essentially rests or oscillates oppositely to the measuring tube. The inner part of the measuring transducer formed by means of measuring tube and counteroscillator is most often held alone by means of the two connecting tubes, via which the measuring tube communicates during operation with the process line, in a protective measuring transducer housing, especially in a manner enabling oscillations of the inner part relative to the measuring transducer housing. In the case of the measuring transducers shown, for example, in U.S. Pat. Nos. A 5,291,792, A 5,796,010, A 5,945,609, B 7,077,014, US-A 2007/0119264, WO-A 01/02 816 and WO-A 99/40 394 with a single, essentially straight measuring tube, the latter and the counteroscillator are, such as quite usual in the case of conventional measuring transducers, oriented essentially coaxially to one another, in that the counteroscillator is embodied as a essentially straight hollow cylinder and is so arranged in the measuring transducer that the measuring tube is at least partially jacketed by the counteroscillator. Especially in the case of application of titanium, tantalum or zirconium, respectively alloys thereof, for the measuring tube, used for the counteroscillator are, most often, comparatively cost effective steel types, such as, for instance, structural steel or free-machining steel.

For actively exciting, respectively maintaining, oscillations of the at least one measuring tube, not least of all also the wanted oscillations, measuring transducers of vibration-type have, additionally, an exciter mechanism formed by means of at least one electromechanical, for example, namely electrodynamic, electrostatic or piezoelectric, oscillation exciter acting during operation differentially on the at least one measuring tube and the, in given cases present, counteroscillator, respectively the, in given cases present, other measuring tube. The oscillation exciter, electrically connected with the mentioned measuring device electronics by means of a pair electrical connecting lines, for example, in the form of connection wires and/or in the form of conductive traces of a flexible circuit board, and operated by an electrical exciter signal generated by the measuring device electronics and correspondingly conditioned, namely at least per se adapted to changing oscillation characteristics of the at least one measuring tube, serves, especially, to transduce an electrical excitation power fed by means of the mentioned exciter signal into a drive force acting at a point of engagement formed by the oscillation exciter on the at least one measuring tube.

The exciter signal is, in such case, especially, so conditioned that the drive force, as a result, has a wanted force component introduced into the measuring tube, namely a periodic force component changing with an excitation frequency corresponding to the wanted frequency and effecting the wanted oscillations. This is typically implemented by providing the mentioned exciter signal with a wanted excitation component, namely a harmonic signal component changing with a signal frequency corresponding to the wanted frequency and having, in comparison with possible additional signal components of other frequencies contained in the exciter signal, a highest signal power.

For the mentioned case, in which resonant oscillations corresponding to the bending oscillation fundamental mode serve as wanted oscillation, respectively the excitation frequency is set exactly to the corresponding resonant frequency, a velocity response of the at least one measuring tube, namely a velocity of the oscillatory movements of the at least one measuring tube time changing with the wanted frequency at the point of engagement, has relative to the wanted force component of the drive force, as is known, no phase shift, consequently the wanted force component of the drive force and the velocity response under resonance condition ($\Re$) lie in phase, respectively under resonance conditions a corresponding phase shift angle between the wanted force component and the velocity response amounts to zero. The exciter signal, in such case, is additionally often also conditioned such that the wanted oscillations have an essentially constant oscillation amplitude, in spite of fluctuating density and/or viscosity. This is typically achieved in the case of density measuring devices of the type being discussed by providing the exciter signal, respectively the wanted excitation component, with an impressed electrical current, namely an electrical current controlled by the measuring device electronics to a predetermined effective value largely independent of possible disturbances, and/or by providing the exciter signal, respectively the wanted excitation component, with an impressed voltage, namely a voltage controlled to a predetermined effective value by the measuring device electronics largely independently of possible disturbances.

Oscillation exciters of usually marketed measuring transducers of the vibration-type are typically constructed in the manner of a type of oscillation coil, namely formed by means of a magnet coil—in the case of measuring transducers with a measuring tube and a counteroscillator coupled therewith most often a magnet coil affixed on the latter—as well as a permanent magnet serving as magnet armature, interacting with the at least one magnet coil, and correspondingly affixed on the measuring tube to be moved. The permanent magnet and the magnet coil are, in such case, usually so oriented that they extend essentially coaxially relative to one another. Additionally, in the case of conventional measuring transducers, the oscillation exciter is most often so embodied and placed that it essentially acts centrally on the at least one measuring tube. Alternatively to an exciter mechanism formed by means of an oscillation exciter acting rather centrally and directly on the measuring tube, it is possible, such as mentioned, among other things, in the above mentioned U.S. Pat. No. 6,092,429, for example, also to use exciter mechanisms formed by means of two oscillation exciters affixed not in the center of the measuring tube, but, instead, rather at the inlet, respectively outlet, sides thereof or, such as, among other things, provided in U.S. Pat. Nos. 6,223,605 or 5,531,126, for example, also exciter mechanisms formed by means of an oscillation exciter acting between the, in given cases present, counteroscillator and the measuring transducer housing. As, among other things, shown in U.S. Pat. No. 6,477,901 or WO-A 00/34748, it is possible alternatively to the aforementioned oscillation exciters of electrodynamic type, however, at times, also to use piezoelectric, seismic or—not least of all also in the case of such a measuring transducer, whose at least one measuring tube has a very small caliber of less than 1 mm—electrostatic oscillation exciters for exciting wanted oscillations.

For registering oscillatory movements of the at least one measuring tube, not least of all also those corresponding to the wanted oscillations, measuring transducers of the type being discussed have, furthermore, at least one oscillation sensor placed on the measuring tube, for example, electrically connected with the measuring device electronics by means of its own pair of electrical connecting lines, and adapted to transduce the oscillatory movements into a oscillation measurement signal representing such and containing a wanted signal component, namely a periodic signal component with a signal frequency corresponding to the wanted frequency, and to provide the oscillation measurement signal to the measuring device electronics, for example, namely a measuring- and operating circuit of the measuring device electronics formed by means of at least one microprocessor, for additional processing. In the case of measuring transducers of usually marketed vibronic density measuring devices, the oscillation sensors are most often, insofar, embodied essentially of equal construction with that of the at least one oscillation exciter, in that they work according to the same principle of action as in the case of an electrodynamic oscillation exciter, for example, thus, in each case, are likewise of electrodynamic type. Accordingly, also the oscillation sensors of such a sensor arrangement are most often likewise, in each case, formed by means of a permanent magnet affixed on the measuring tube and at least one coil-, for example, a coil affixed on the, in given cases present, other measuring tube or on the, in given cases present, counteroscillator—permeated by a magnetic field of the permanent magnet and as a result of the oscillatory movements of the at least one measuring tube supplied at least at times with an induced measurement voltage. However, also optically or also capacitively designed oscillation sensors are equally usual for oscillation measurement, for example, even for the case, in which the oscillation exciter is of electrodynamic type.

The fulfillment of the resonance condition ($\Re$) essential in the case of conventional vibronic density measuring devices for measuring the density can during operation, for example, be recognized by the respective measuring device electronics noting that a phase shift angle between wanted excitation component and wanted signal component has achieved a predetermined phase value, namely one corresponding to the above referenced resonance condition, in the case of which the phase shift angle between the velocity response and the wanted force component of the drive force is zero, and remains, at least for a predetermined interval, namely for a time sufficiently long for measuring the density, essentially constant. In order to implement a highly accurate measuring of the density also for media with a density variable within a broad density measurement range and/or changing quickly with time, consequently to provide a density measuring device with an as high as possible dynamic range, the measuring device electronics of measuring devices of the type being discussed are not least of all also adapted so to condition the exciter signal that the excitation frequency of the wanted force component corresponds during the measuring of the density as exactly as possible to a respective instantaneous resonant frequency, for example, thus that of the mentioned bending oscillation fundamental mode, respectively that the excitation frequency is adjusted as quickly as possible to a possibly changed resonant frequency, for instance, as a result of a fluctuating density and/or a fluctuating temperature of the measuring tube. The adjusting of the wanted force component by means of the measuring device electronics occurs in the case of conventional density measuring devices typically with exploitation of the above referenced resonance condition, in such a manner that by means of the at least one oscillation measurement signal-, for example, namely based on its wanted signal component—as well as by means of the exciter signal-, for example, namely by setting the signal frequency of the wanted excitation component—the excitation frequency of the wanted force component is changed continuously, respectively successively, and, indeed, to the extent that, respectively until, the phase shift angle between wanted excitation component and wanted signal component has achieved the predetermined phase value, for example, thus is approximately zero. Electronic circuits suitable for setting, respectively tracking, the wanted frequency of the respective measuring tube to one of its instantaneous resonant frequencies, —for example, an electronic circuit configured as a phase locked loop (PLL) respectively frequency control methods implemented therewith, are known, per se, to those skilled in the art, for example, from the above mentioned U.S. Pat. No. A 4,801,897, respectively US-A 2010/0005887.

Due to the wanted oscillations of the at least one measuring tube, —not least of all also for the case, in which the wanted oscillations of the at least one measuring tube are bending oscillations—there can, as is known, be induced in the flowing medium Coriolis forces also dependent on the instantaneous mass flow rate. These, in turn, can bring about Coriolis oscillations with wanted frequency superimposed on the wanted oscillations and dependent on the mass flow rate, in such a manner that a travel time-, respectively phase difference, also dependent on the mass flow rate, consequently also usable as a measure for the mass flow measurement, can be detected between inlet-side and outlet-side oscillatory movements of the at least one measuring tube performing wanted oscillations and at the same time flowed-through by the medium. In the case of an at least sectionally curved measuring tube, in the case of which there is selected for the wanted oscillations an oscillation form, in which the measuring tube is caused to move like a pendulum in the manner of a cantilever clamped on one end, the resulting Coriolis oscillations correspond, for example, to that bending oscillation mode-, at times, also referenced as a twist mode-, in which the measuring tube executes rotary oscillations about an imaginary rotary oscillation axis directed perpendicular to the imaginary oscillation axis, while, in contrast, in the case of a straight measuring tube, whose wanted oscillations are embodied as bending oscillations in a single imaginary plane of oscillation, the Coriolis oscillations are, for example, bending oscillations essentially coplanar with the wanted oscillations. For the above already mentioned case, in which the density measuring device should supplementally to the density additionally also ascertain the mass flow rate of the respective medium guided in the measuring transducer, measuring transducers of the type being discussed have for the purpose of the registering both inlet-side as well as also outlet-side oscillatory movements of the at least one measuring tube and for producing at least two electrical oscillation measurement signals influenced by the mass flow rate to be measured, furthermore, most often two or more oscillation sensors spaced from one another along the measuring tube and so embodied and arranged, that the oscillation measurement signals generated therewith and fed to the measuring device electronics have not only, such as already mentioned, in each case, a wanted signal component, but, instead, that additionally also between the wanted signal components of both oscillation measurement signals a travel time-, respectively phase difference, dependent on the mass flow rate is measurable. Alternatively or supplementally to measuring also the mass flow rate supplementally to the measuring of the density, it is—such as already mentioned, respectively shown, among other things, in the above mentioned US-A 2011/0265580—additionally also possible directly to measure by means of such measuring transducer of vibration-type, consequently by means of vibronic density measuring devices formed therewith, supplementally also a viscosity of the through flowing medium, for example, based on an electrical excitation power required for exciting, respectively maintaining, the wanted oscillations, respectively based on a damping of the wanted oscillations ascertained based on the excitation power, and to output such in the form of qualified viscosity measured values.

In the case of vibronic density measuring devices of the type being discussed, the ascertaining of the density occurs, such as already mentioned, typically based on actively excited, resonant oscillations of the at least one measuring tube, especially namely based on a measuring of at least one of its instantaneous resonance frequencies. The respective measuring device electronics of conventional vibronic density measuring devices is accordingly also adapted, based on the wanted signal component won from the at least one oscillation measurement signal generated under resonance condition ($\Re$), recurringly to ascertain a frequency measured value, which represents the respectively current, wanted frequency, consequently the current resonant frequency of the at least one measuring tube, and thereafter with application of one or more mentioned frequency measured values to generate a, typically, first of all, digital, density measured value representing the density of the respective medium, for example, by the performing of corresponding calculating algorithms by the mentioned microprocessor. Since the oscillation characteristics of the at least one measuring tube, not least of all also its respective resonance frequencies, and, associated therewith, density accuracy of measurement, namely an accuracy of measurement, with which the density can be measured, are, as is known, dependent also on a temperature distribution within the respective tube wall of the at least one measuring tube, typically at least also a measuring tube temperature is taken into consideration in the case of such density measurements. This is perceivable, among others, from the above mentioned U.S. Pat. No. A 4,491,009, WO-A 88/02853, WO-A 98/02725 or WO-A 94/21999. For ascertaining temperature, at least one local temperature of the at least one measuring tube on a surface of the tube wall facing away from its lumen is registered by sensor, typically by means of a platinum-resistance of a resistance thermometer or a thermocouple adhered on the surface and electrically connected with the respective measuring device electronics, and the measuring device electronics is, furthermore, adapted, based on a temperature signal representing the temperature of the at least one measuring tube, during operation recurringly to ascertain a temperature measured value representing a temperature of the tube wall and to use such temperature measured value in the calculating of the density, not least of all for the purpose of lessening cross-sensitivity of the density measuring device to temperature influences. The actual measuring of the density occurs in the case of conventional density measuring devices of the aforementioned type ultimately, once the measuring device electronics has detected fulfillment of the resonance condition, by ascertaining by means of the measuring device electronics based on the wanted signal component, for example, extracted by means of a digital signal filter from the at least one oscillation measurement signal, first of all, at least one frequency measured value representing the resonant frequency serving as wanted frequency and then converting the frequency measured value into the corresponding density measured value, namely instantaneously representing the density. The converting of the frequency into the associated density measured value can occur, for example, by forming a reciprocal of a square of the frequency measured value and combining the same together with a corresponding temperature measured value for the instantaneous temperature of the tube wall using a characteristic line function correspondingly furnished in the measuring device electronics—for example, in the form of a calculation algorithm executed by the mentioned microprocessor.

Further improvement of the accuracy of the density measurement in the case of vibronic density measuring devices of the aforementioned type can additionally also be achieved, such as, among other things, also disclosed in the above mentioned US-A 2004/0123645, US-A 2011/0219872, WO-A 94/21999, WO-A 98/02725, when, for the purpose of correcting possible further dependencies of the resonant frequency on other medium-, respectively flow specific, measured variables, such as, for instance, a mass flow rate of the medium flowing in the at least one measuring tube, respectively a pressure reigning within the medium guided in the at least one measuring tube, and/or for the purpose of correcting for possible changes of measuring transducer specific, oscillation characteristics, for instance, as a result of an additional, at times, also irreversible, deformation of the at least one measuring tube located in the static resting position and caused by changed temperature distribution within the tube wall or caused by (clamping-) forces acting on the at least one measuring tube, respectively therefrom resulting additional mechanical stresses within the measuring transducer, corresponding influencing variables are metrologically registered and correspondingly taken into consideration in the calculating of the density, for instance, by conforming corresponding correction terms with the previously indicated characteristic line function. Mechanical deformations of the at least one measuring tube can, as well as also disclosed in the above mentioned US-A 2011/0219872, be registered, for example, by means of one or more strain sensors mechanically coupled with the measuring tube on its surface facing away from the lumen.

Further investigations have, furthermore, shown that additionally also the damping of the wanted oscillations effected by dissipation of oscillatory energy into heat is another influencing variable, which can influence the resonant frequency serving as wanted frequency to a not directly negligible extent, respectively can likewise represent a certain cross-sensitivity for the density measuring device. Since changes of the damping as well as, associated therewith, changes of the corresponding resonant frequency in the case of intact measuring transducer in considerable measures are also determined by changes of the viscosity of the respective medium to be measured, in such a manner that the particular resonant frequency in the case of increasing viscosity decreases, in spite of density remaining constant, there is an opportunity for correction of such changes of the resonant frequency caused by changes of the damping. This is done, first of all, basically by having the measuring device electronics ascertain the viscosity—for example, such as already mentioned, based on an electrical excitation power required for exciting, respectively maintaining, the wanted oscillations—and represent such in at least one viscosity measured value instantaneously representing such and/or in at least one damping value representing a damping of the wanted oscillations dependent thereon, in order thereafter to ascertain the density measured value with application also of the viscosity measured value, respectively the damping value, as well as a correspondingly expanded characteristic line function, namely a characteristic line function also taking into consideration the change of the resonant frequency effected by changes of the viscosity. A disadvantage of such a correction based on measuring the viscosity of the medium guided in the at least one measuring tube, respectively a damping of the wanted oscillations dependent thereon, is not least of all that the damping not only depends on the viscosity but, instead, to a certain degree additionally also on the actually to be measured, consequently, first of all, unknown, density of the medium. As a result of this, also the density measured values ascertained by applying viscosity-, respectively damping, values generated by means of the measuring device electronics can, in fact, still have considerable, in given cases, even intolerable, measurement errors.

SUMMARY OF THE INVENTION

An object of the invention, consequently, is to provide a vibronic density measuring device formed by means of at least one measuring tube, which has no, or only a negligibly low, dependence of the density accuracy of measurement on damping of the wanted oscillations, respectively a viscosity of the medium causing such.

For achieving the object, the invention resides in a density measuring device, for example, a Coriolis mass flow/density measuring device and/or a density-/viscosity measuring device, for measuring density of a flowable medium, for example, a gas or a liquid, respectively for measuring density of a medium flowing in a pipeline, for example, a gas or a liquid, which density measuring device comprises a measuring device electronics as well as a measuring transducer electrically connected with the measuring device electronics and having at least one measuring tube, for example, an at least sectionally straight and/or at least sectionally curved, measuring tube, an oscillation exciter, for example, an electrodynamic, electrostatic or piezoelectric, oscillation exciter, for exciting and maintaining oscillations of the at least one measuring tube, and a first oscillation sensor, for example, an electrodynamic or electrostatic, first oscillation sensor, for registering oscillations of the at least one measuring tube. The measuring tube of the density measuring device of the invention has a lumen surrounded by a tube wall and is adapted to guide medium in its lumen and during that to be caused to vibrate in such a manner that the measuring tube executes wanted oscillations, namely mechanical oscillations, for example, bending oscillations, about a resting position with a wanted frequency, for example, a wanted frequency co-determined by the density of the medium. Additionally, the first oscillation sensor of the density measuring device of the invention, for example, a first oscillation sensor spaced from the oscillation exciter along the measuring tube, is adapted to register oscillatory movements of the at least one measuring tube and to transduce such into a first oscillation measurement signal representing such, especially a first oscillation measurement signal namely having a signal frequency corresponding to the wanted frequency, and the measuring device electronics is adapted, by means of an exciter signal, especially an exciter signal having namely a signal frequency corresponding to the wanted frequency, to supply electrical power into the oscillation exciter, wherein the oscillation exciter, in turn, is adapted, by means of the exciter signal, to transduce supplied electrical power into a drive force acting on a point of engagement of the oscillation exciter on the at least one measuring tube, wherein the drive force has a wanted force component introduced into the measuring tube, namely a periodic force component changing with an excitation frequency corresponding to the wanted frequency and effecting the wanted oscillations. In the case of the density measuring device of the invention, the measuring device electronics is, furthermore, adapted, by means of the first oscillation measurement signal as well as the exciter signal, to adjust the drive force, for example, namely the wanted force component, respectively its excitation frequency, in such a manner that during a predetermined, for example, not less than 10 ms, phase control interval a phase shift angle, for example, a constant phase shift angle, by which a velocity response of the at least one measuring tube, namely a velocity of the oscillatory movements of the at least one measuring tube at the point of engagement changing with the wanted frequency as a function of time, is phase shifted from the wanted force component of the drive force is less than −20° and greater than −80°, for example, is less than −30° and/or greater than −70°, and/or the wanted frequency has a frequency value, which corresponds to greater than 1.00001-times, equally as well less than 1.001-times, a frequency value of a, for example, lowest, instantaneous resonant frequency of the at least one measuring tube. Based on the first oscillation measurement signal present during the phase control interval, the measuring device electronics ascertains, furthermore, at least one frequency measured value, which represents the wanted frequency for the mentioned phase control interval, in order thereafter with application of the mentioned frequency measured value to generate a density measured value representing the density.

In a first embodiment of the invention, the measuring device electronics is adapted to adjust the drive force, respectively its wanted force component, by changing a signal frequency of the exciter signal.

In a second embodiment of the invention, the measuring device electronics is adapted to bring the phase shift angle during the total phase control interval and/or for a duration of greater than 10 ms to a predetermined desired phase value, for example, in such a manner that the phase shift angle in the case of constant density fluctuates by less than ±1% of the mentioned desired phase value and/or by less than ±2° around the mentioned desired phase value.

In a third embodiment of the invention, it is provided that the measuring device electronics has a phase locked loop (PLL), for example, a digital, phase locked loop (PLL), for setting the phase shift angle.

In a fourth embodiment of the invention, the measuring device electronics is adapted to change the signal frequency of the exciter signal until the phase shift angle has achieved a predetermined desired phase value, for example, namely in such a manner that the measuring device electronics in the case of a too small phase shift angle, namely a phase shift angle set less than the desired phase value, lessens the signal frequency, and in such a manner that the measuring device electronics in the case of a too large phase shift angle, namely a phase shift angle set greater than the desired phase value, increases the signal frequency.

In a fifth embodiment of the invention, the measuring tube is adapted to be flowed through by the medium with a mass flow rate during execution of the wanted oscillations, for example, namely in order to induce in the flowing medium Coriolis forces dependent on its mass flow rate, which Coriolis forces are suitable to bring about Coriolis oscillations superimposed on the wanted oscillations and of equal frequency thereto.

In a sixth embodiment of the invention, it is provided that the measuring transducer has a second oscillation sensor spaced along the measuring tube from the first oscillation sensor, for example, a second oscillation sensor constructed equally to the first oscillation sensor, for registering oscillations, for example, outlet-side oscillations, of the at least one measuring tube, and that the second oscillation sensor is adapted to register oscillatory movements of the at least one measuring tube and to transduce such into a second oscillation measurement signal representing such; especially namely in such a manner that the second oscillation measurement signal has a signal frequency corresponding to the wanted frequency. Developing this embodiment of the invention further, it is, furthermore, provided that the measuring device electronics ascertains the frequency measured value based on both the first oscillation measurement signal as well as also the second oscillation measurement signal and/or that the measuring device electronics adjusts the wanted force component also by means of the second oscillation measurement signal. Alternatively thereto or in supplementation thereof, the measuring tube is, furthermore, adapted to be flowed through by the medium with a mass flow rate during execution of the wanted oscillations, in order to induce in the flowing medium Coriolis forces dependent on its mass flow rate, which Coriolis forces are suitable to bring about Coriolis oscillations superimposed on the wanted oscillations and of frequency equal thereto, in such a manner that between the first oscillation measurement signal and the second oscillation measurement signal a phase difference exists dependent on the mass flow rate. Based on both the first oscillation measurement signal as well as also the second oscillation measurement signal, the measuring device electronics can, thus, also generate a mass flow measured value representing the mass flow rate, for example, in that the measuring device electronics, especially namely during the phase control interval, ascertains based on the first oscillation measurement signal and the second oscillation measurement signal, first of all, a phase difference measured value, which represents the phase difference dependent on the mass flow rate, and that the measuring device electronics generates the mass flow measured value thereafter based on the phase difference measured value.

In a seventh embodiment of the invention, the measuring device electronics is adapted outside of the phase control interval to adjust the wanted force component, for example, its excitation frequency, at least temporarily, for example, during a starting up of the density measuring device and/or for checking its ability to function and/or after a change of a resonant frequency of the measuring tube by greater than 1 Hz, in such a manner that the phase shift angle amounts to not less than −5° and no greater than +5°, for example, not less than −2° and/or no greater than +2°, for example, in such a manner that the excitation frequency of the wanted force component corresponds to a resonant frequency of the at least one measuring tube, consequently the wanted oscillations of the at least one measuring tube are resonant oscillations.

In an eighth embodiment of the invention, the measuring device electronics is adapted outside of the phase control interval to adjust the wanted force component, for example, its excitation frequency, at least temporarily, for example, during a starting up of the density measuring device and/or for checking its ability to function, in such a manner that the wanted oscillations of the at least one measuring tube at times are resonant oscillations, consequently the wanted frequency corresponds at times to a resonant frequency of the at least one measuring tube.

In a ninth embodiment of the invention, the measuring transducer is s produced in microsystem technology.

In a tenth embodiment of the invention, it is provided that the tube wall of the at least one measuring tube is composed of silicon.

In an 11$^{th}$ embodiment of the invention, it is provided that the tube wall of the at least one measuring tube is composed of titanium, respectively a titanium-alloy.

In a twelfth embodiment of the invention, it is provided that the tube wall of the at least one measuring tube is composed of tantalum, respectively a tantalum-alloy.

In a 13$^{th}$ embodiment of the invention, it is provided that the tube wall of the at least one measuring tube is composed of zirconium, respectively a zirconium-alloy.

In a 14$^{th}$ embodiment of the invention, it is provided that the tube wall of the at least one measuring tube is composed of a nickel based alloy.

In a 15$^{th}$ embodiment of the invention, it is provided that the at least one measuring tube has a caliber, which is less than 1 mm, for example, less than 0.5 mm.

In a 16$^{th}$ embodiment of the invention, it is provided that the tube wall of the at least one measuring tube is composed of a metal, for example, a stainless steel.

In a 17$^{th}$ embodiment of the invention, it is provided that the at least one measuring tube has a caliber, which is greater than 1 mm, for example, greater than 10 mm.

In an 18$^{th}$ embodiment of the invention, the measuring device electronics is adapted based on the first oscillation measurement signal and/or the exciter signal to generate a viscosity measured value, which represents a viscosity of the medium.

In a first further development of the invention, such additionally comprises, thermally coupled with the at least one measuring tube, a temperature sensor, which is adapted to register a temperature of the at least one measuring tube and to transduce such into a temperature measurement signal representing such, and the measuring device electronics is, furthermore, adapted, by means of the temperature measurement signal, to ascertain at least one temperature measured value, which represents a temperature of the at least one measuring tube, as well as to generate the density measured value with application also of the temperature measured value.

In a second further development of the invention, such additionally comprises, mechanically coupled with the at least one measuring tube, a strain sensor, which is adapted to register a strain of the at least one measuring tube and to transduce such into a strain measurement signal representing such, and the measuring device electronics is, furthermore, adapted, by means of the strain measurement signal, to a certain at least one strain measured value, which represents a strain of the at least one measuring tube, respectively a mechanical stress within the at least one measuring tube, for example, as a result of a deformation of the measuring transducer causing the strain, as well as to generate the density measured value with application also of the strain measured value.

A basic idea of the invention is to improve the accuracy of measurement of vibronic density measuring devices of the type being discussed, wherein, for the purpose of measuring density, mechanical oscillations of the at least one measuring tube are excited as wanted oscillations with a wanted frequency differing from the instantaneous resonant frequency, in such a manner that the phase shift angle between the velocity response and the drive force wanted force component effecting the wanted oscillations is held for a required density measurement time interval significantly different from zero, namely during a phase control interval correspondingly required for controlling the phase shift angle (as well as for the measuring of the actual wanted frequency) to a phase value lying within a phase angle wanted interval, which ranges from −20° to −80, indeed a phase angle which is then held as constant as possible. The ascertaining of the density occurs accordingly thus based on wanted oscillations, at which the resonance condition is actually not fulfilled, respectively at which the wanted frequency has a frequency value, which is greater than 1.00001-times, equally as well less than 1.001-times a frequency reference value, namely an instantaneous frequency value of a reference resonant frequency, namely a reference resonant frequency in the form of a respectively nearest neighboring resonant frequency, for example, thus the resonant frequency of the bending oscillation fundamental mode. For the mentioned typical case, for instance, that in which bending oscillations corresponding to the bending oscillation fundamental mode should serve as wanted oscillations and the resonant frequency of the bending oscillation fundamental mode lies, for instance, at 1000 Hz, the wanted frequency would be set, thus, at 1000.01 Hz to 1001 Hz, consequently a corresponding frequency shift, by which the wanted frequency is increased from the reference resonant frequency, would lie, for instance, in the range between 0.01 Hz to 1 Hz.

The invention is based, among other things, on the surprising discovery that within this phase angle wanted interval lying between −20° and −80°, which is basically avoided in the case of conventional density measuring devices for measuring density as well as also for the possible measuring of the mass flow, a phase shift angle exists, in given cases, also a measurement device- or measurement device type specific, phase shift angle, at which the dependence of the wanted frequency on the damping of the wanted oscillations, respectively the viscosity of the respective medium to be measured effecting the damping, is minimal, in any event, however, in comparison to the mentioned dependence at resonance, is significantly smaller.

It has, furthermore, been found that in the case of exciting of the wanted oscillations in the previously indicated phase angle range, indeed, the amplitude can sink to a considerable degree, namely by more than 50%, in comparison to the amplitude under resonance conditions at otherwise equal excitation power—not least of all because of the regularly very high quality factors (Q) in the case of measuring transducers of the type being discussed for natural bending oscillation modes of the at least one measuring tube, especially namely also its bending oscillation fundamental mode, of greater than 1000 (Q>1000), respectively regularly very low bandwidths (B) for bending oscillation modes of less than one hundredth of a respective resonant frequency-, that surprisingly, however, nevertheless, by evaluation of the corresponding Coriolis oscillations, namely Coriolis oscillations generated not under resonance conditions, a still high accuracy of measurement can be achieved for the mass flow measurement; this surprisingly even also with the established measurements technology installed in conventional Coriolis mass flow/density measuring devices, namely both by means of conventional measuring transducers as well as also by means of such measuring device electronics, which, indeed, are modified for the purpose of implementing the invention as regards corresponding specification-, respectively desired values, not least of all also for the control implemented therewith for setting amplitude and frequency of the wanted oscillations, compared with measuring device electronics of conventional density measuring devices, which otherwise, however, as regards the construction in principle and its operation in principle can largely correspond to measuring device electronics of conventional density measuring devices.

BRIEF DESCRIPTION OF THE DRAWINGS

The invention as well as other advantageous embodiments thereof will now be explained in greater detail based on examples of embodiments shown in the figures of the drawing. Equal parts are provided in all figures with equal reference characters; when perspicuity requires or it otherwise appears sensible, already mentioned reference characters are omitted in subsequent figures. Other advantageous embodiments or further developments, especially also combinations, first of all, of only individually explained aspects of the invention, result, furthermore, from the figures of the drawing, as well as also the dependent claims per se. The figures of the drawing show as follows:

DETAILED DISCUSSION IN CONJUNCTION WITH THE DRAWINGS

Figures 1, 2:
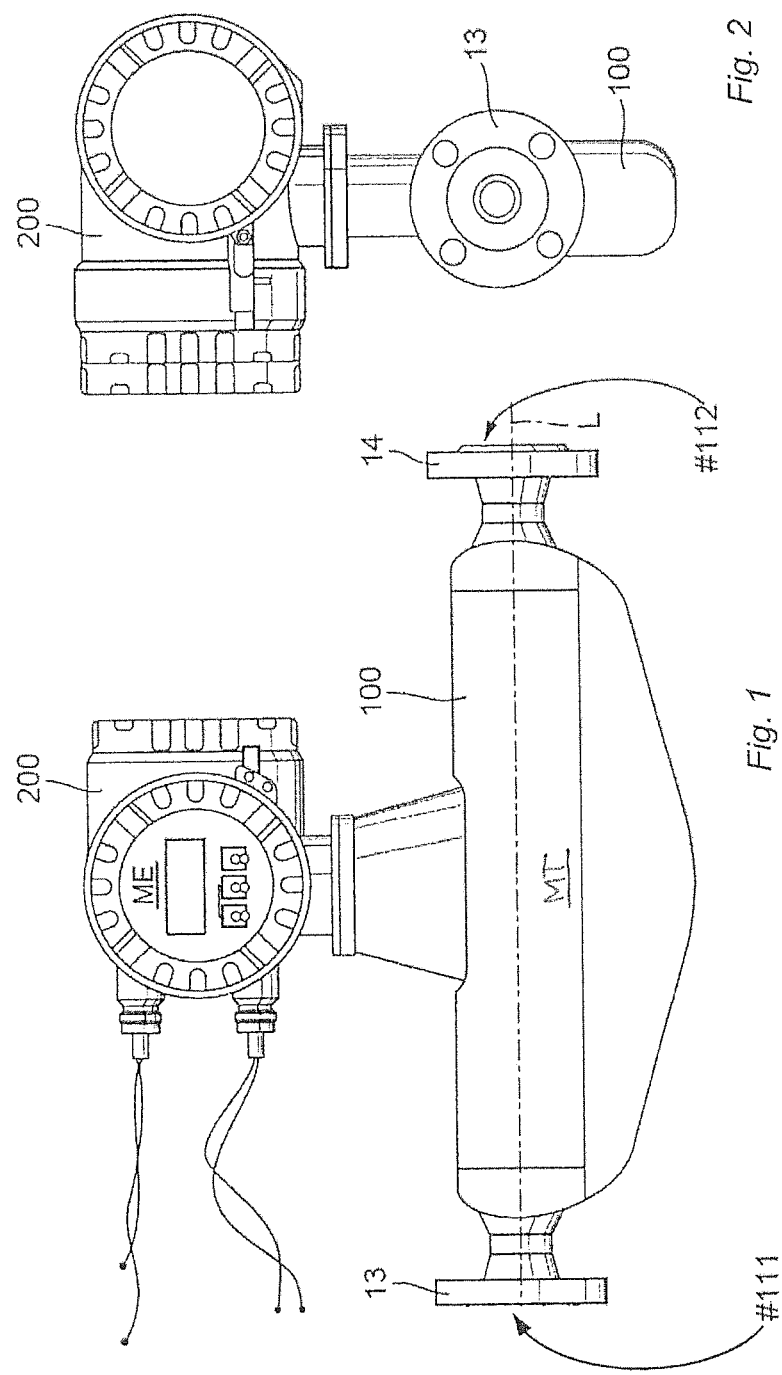
FIGS. 1 and 2 are side and end views of an example of an embodiment of a density measuring device, especially a density measuring device suitable for application in industrial measuring- and automation technology, with a measuring transducer of vibration-type having a measuring transducer housing and a measuring device electronics accommodated in an electronics housing secured on the measuring transducer housing.

FIGS. 1 and 2 show schematically in different side views a density measuring device for measuring density of a medium, especially a liquid or a gas, flowing in a process line (not shown), respectively for recurring ascertaining of measured values ($X_\rho$) instantaneously representing density. In an additional embodiment of the invention, the density measuring device is, furthermore, provided, supplementally also to measure viscosity of the medium, respectively to ascertain measured values ($X_\eta$) correspondingly representing such. Alternatively thereto or in supplementation thereof, the density measuring device can, furthermore, also be adapted to ascertain for the medium flowing in the pipeline a mass flow, namely a total mass flowed during a predeterminable or earlier determined, measurement interval and/or a mass flow rate, respectively to ascertain measured values ($X_m$) correspondingly representing such.

The density measuring device comprises a measuring transducer MT of vibration-type connectable, respectively connected, via an inlet end #111 as well as an outlet end #112 to the process line embodied, for example, as a pipeline, which measuring transducer is flowed through during operation correspondingly by the medium to be measured, a medium such as, for instance, a low viscosity liquid and/or a high viscosity paste and/or a gas. The measuring transducer MT serves, in general, to produce in the respectively flowing medium mechanical reaction forces, namely, especially, inertial forces dependent on density, however, in given cases, also Coriolis forces dependent on mass flow and/or frictional forces dependent on viscosity, which react registerably by sensor, consequently measurably, on the measuring transducer. Derived from these reactions forces, then, e.g. density ρ and, in given cases, also the mass flow m and/or the viscosity η of the medium can be measured. The measuring transducer MT is, furthermore, adapted to generate at least one primary signal, which has at least one characteristic signal parameter dependent on density, especially namely a signal frequency dependent on density and/or a signal amplitude dependent on density and/or a phase angle dependent on density. Furthermore, the density measuring device comprises a measuring device electronics ME electrically connected with the measuring transducer MT, especially a measuring device electronics ME supplied during operation with electrical energy externally via a connection cable and/or by means of an internal energy storer, for producing measured values ($X_\rho$) representing density, respectively for outputting such a measured value to a corresponding measurement output as a currently valid measured value of the density measuring device. The measuring device electronics ME, e.g. one formed by means of at least one microprocessor and/or by means of a digital signal processor (DSP), can, such as indicated in FIG. 1, be accommodated, for example, in a single, in given cases, also chambered, electronics housing 200 of the density measuring device. Said electronics housing 200 can, depending on requirements of the density measuring device, for example, also be embodied impact- and/or also explosion resistantly and/or hermetically sealedly.

Figure 3:
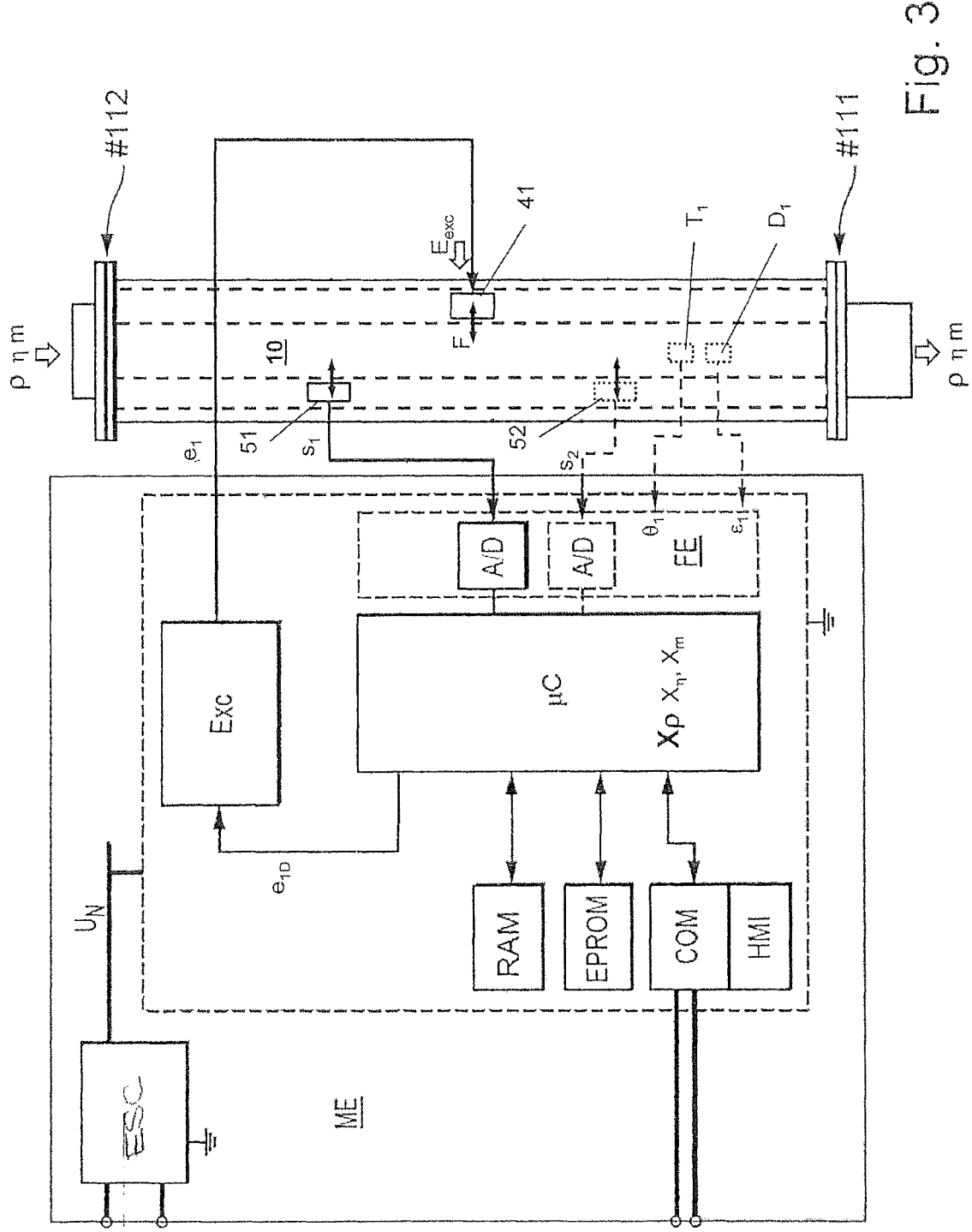
FIG. 3 shows schematically in the manner of a type of block diagram, an example of an embodiment of a measuring device electronics suitable for a density measuring device according to FIGS. 1 and 2.

The measuring device electronics ME includes, such as shown schematically in FIG. 3 in the manner of a type of block diagram, a driver circuit Exc serving for activating the measuring transducer as well as a measuring- and evaluating circuit μC processing primary signals of the measuring transducer MT, for example, a measuring- and evaluating circuit μC formed by means of a microprocessor and/or communicating during operation with the driver circuit Exc. The measuring- and evaluating circuit μC generates during operation measured values representing at least density, in given cases, however, also the instantaneous or totaled mass flow and/or the viscosity. Furthermore, the measuring device electronics can also be so embodied that as regards circuit construction it corresponds to one of the measuring device electronics known from the above the state of the art, for example, U.S. Pat. No. B 6,311,136, or, for example, also corresponds to a measurement transmitter of a Coriolis mass flow/-density measuring device offered by the applicant, e.g. under the designation "PROMASS 83F", respectively at http://www.de.endress.com/#product/83F.

The measured values generated by means of the measuring device electronics ME can in the case of the here shown density measuring device be displayed, for example, also on-site, namely directly at the measuring point formed by means of the density measuring device. For visualizing on-site measured values produced by means of the density measuring device and/or, in given cases, measuring device internally generated system status reports, such as, for instance, an increased measurement accuracy, respectively an error report signaling uncertainty or an alarm signaling a disturbance in the density measuring device or at the measuring point formed by means of the density measuring device, the density measuring device can have, as well as also indicated in FIG. 1, for example, a display- and servicing element HMI communicating with the measuring device electronics, in given cases, also a portable, display- and servicing element HMI, such as, for instance, an LCD-, OLED- or TFT display placed in the electronics housing 200 behind a window correspondingly provided therein, as well as corresponding input keypad and/or touch screen.

In an advantageous manner, the, for example, also (re-)programmable-, respectively remotely parameterable, measuring device electronics ME can additionally be so designed that during operation of the density measuring device it can exchange with a electronic data processing system superordinated to it, for example, a programmable logic controller (PLC), a personal computer and/or a work station, via a data transmission system, for example, a fieldbus system, such as, for instance, a FOUNDATION FIELDBUS or PROFIBUS fieldbus system, and/or wirelessly per radio, measuring- and/or other operating data, such as, for instance, current measured values, system diagnosis values, system status reports or even values in the form of settings serving for control of the density measuring device. As in the case of the example of an embodiment shown in FIG. 3, especially the measuring- and evaluating circuit μC can be implemented by means of a microcomputer provided in the measuring device electronics ME, for example, by means of a microprocessor, respectively a digital signal processor (DSP), and by means of program-code correspondingly implemented and transpiring therein. The program-code, as well as, serving for control of the density measuring device, other operating parameters, such as e.g. also desired values for controllers, respectively control algorithms, implemented by means of the measuring device electronics, can be stored persistently e.g. in a non-volatile data memory EEPROM of the measuring device electronics ME and upon the starting of the same be loaded into a volatile data memory RAM, e.g. one integrated in the microcomputer. Microprocessors suitable for such applications are available commercially, an example being type TMS320VC33 of the firm Texas Instruments Inc.

Furthermore, the measuring device electronics ME can be so designed that it can be fed from an external energy supply, for example, also via the aforementioned fieldbus system. Moreover, the measuring device electronics ME can, for example, have an internal energy supply circuit ESC for providing internal supply voltages UN. The internal energy supply circuit ESC is fed via the aforementioned fieldbus system during operation by an external energy supply provided in the aforementioned data processing system. In such case, the density measuring device can be embodied, for example, as a so-called four conductor device, in the case of which the internal energy supply circuit of the measuring device electronics ME can be connected by means of a first pair of lines with an external energy supply and the internal communication circuit of the measuring device electronics ME can be connected by means of a second pair of lines with an external data processing circuit or an external data transmission system. The measuring device electronics can, furthermore, however, also be so embodied that, such as, among other things, also shown in the above mentioned U.S. Pat. No. B 7,200.503, U.S. Pat. No. B 7,792,646, it is electrically connectable by means of a two-conductor connection, for example, a two-conductor connection configured as a 4-20 mA electrical current loop, with the external electronic data processing system and by way of that be supplied with electrical energy as well as transmit measured values to the data processing system. For the typical case, in which the density measuring device is equipped for coupling to a fieldbus- or other electronic communication system, the measuring device electronics ME, for example, also an on-site measuring device electronics ME and/or a measuring device electronics ME (re-)programmable via the communication system, can additionally have a corresponding communication interface COM—for example, one conforming to relevant industry standards, such as, for instance, IEC 61158/IEC 61784, —for data communication, e.g. for sending measuring- and/or operating data, consequently measured values representing density and, in given cases, also viscosity and mass flow, respectively measured values representing mass flow rate, to the above mentioned programmable logic controller (PLC) or to a superordinated process control system and/or for receiving settings data for the density measuring device.

Figure 4:
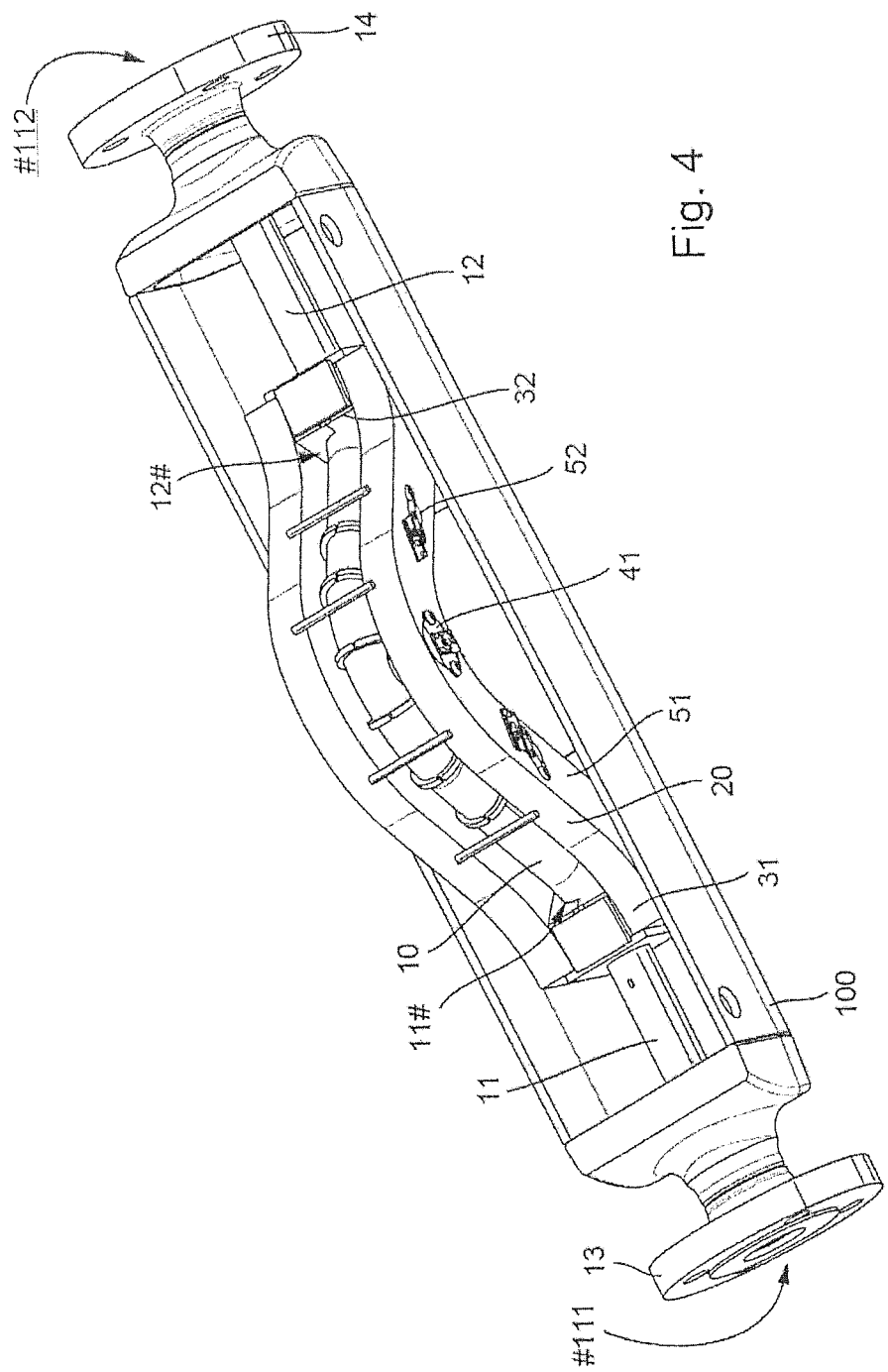
FIGS. 4 and 5 show in different side views, an example of an embodiment of a measuring transducer of vibration-type suitable for a density measuring device of FIGS. 1 and 2 and having a measuring tube.
Figure 5:
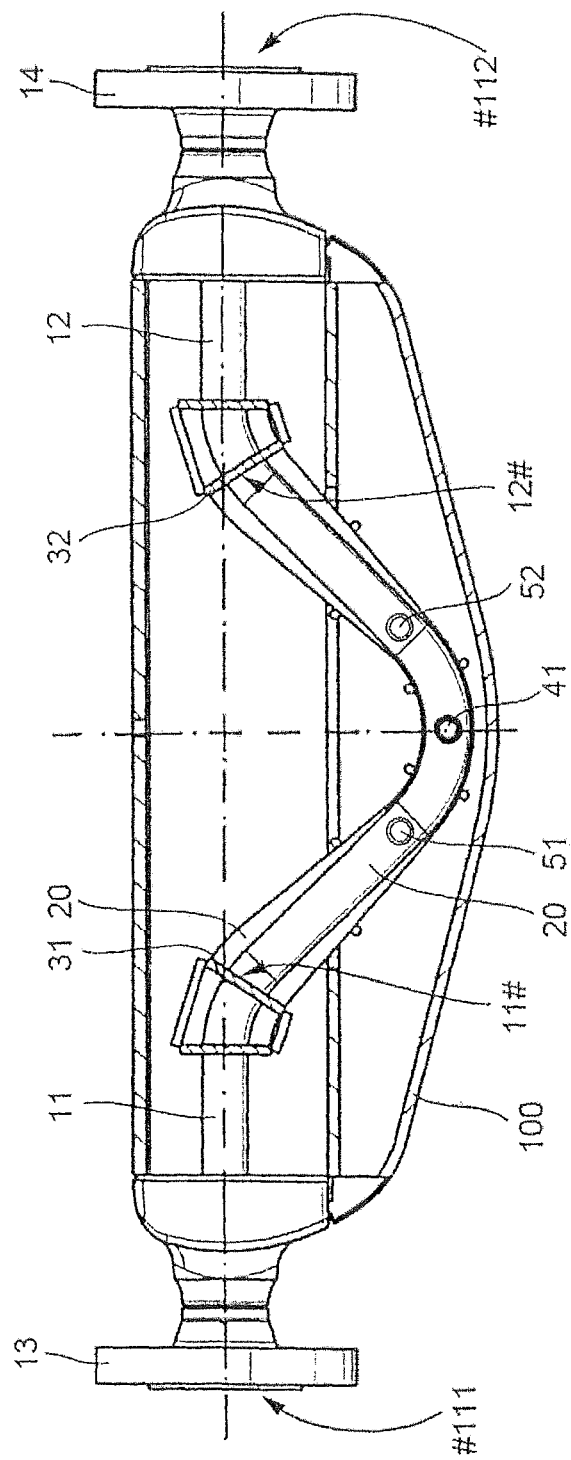

The electrical connecting of the measuring transducer to the measuring device electronics can occur by means of corresponding connecting lines, which extend from the electronics housing 200, for example, via electrical cable guide or feedthrough, into a measuring transducer housing 100 of the measuring transducer and at least sectionally within the measuring transducer housing 200. The connecting lines can be embodied, in such case, at least partially as electrical line wires encased at least sectionally in electrical insulation, e.g. in the form of "twisted-pair" lines, flat ribbon cables and/or coaxial cables. Alternatively thereto or in supplementation thereof, the connecting lines can at least sectionally also be formed by means of conductive traces of a circuit board, for example, a flexible circuit board, in given cases, also lacquered circuit board; compare, for this, also the above patents, U.S. Pat. No. B 6,711,958 and U.S. Pat. No. A 5,349,872. FIGS. 4 and 5 show schematically an example of an embodiment of a measuring transducer MT of vibration-type suitable for implementing the density measuring device of the invention. The measuring transducer comprises an inner part arranged in a measuring transducer housing 100 and serving for effecting a physical to electrical transducing of density and, in given cases, also viscosity, respectively the mass flow rate. Said measuring transducer housing 100, serving not least of all also as a protective shell hermetically sealing the interior of the measuring transducer MT from the surrounding atmosphere, in given cases, also providing a pressure- and/or explosion resistant enclosure, can be manufactured, for example, of a—smooth or also corrugated—stainless steel sheet or even a synthetic or plastic material. Furthermore, the measuring transducer housing 100 can, as well as also indicated in FIG. 1, have a connection nozzle, on which the electronics housing 200 is mounted in the case of a measuring device of compact construction. Arranged within the connection nozzle can be, furthermore, a hermetically sealed and/or pressure resistant feedthrough manufactured, for example, by means of glass- and/or plastic potting compound, for electrical connecting lines extending between the measuring device electronics and the measuring transducer.

For guiding the flowing medium, the inner part, consequently the measuring transducer MT formed therewith, comprises, in principle, at least one measuring tube 10 having a lumen surrounded by a tube wall. Present in the example of an embodiment shown in FIGS. 4 and 5 is a single, at least sectionally curved, measuring tube 10. The tube wall of the at least one measuring tube can be composed, for example, of a metal, for instance, titanium, respectively a titanium alloy, tantalum, respectively a tantalum alloy, zirconium, respectively a zirconium alloy, a stainless steel or a nickel based alloy, or, for example, even silicon. The at least one measuring tube 10 extends, such as evident from FIGS. 4 and 5, with an oscillatory length between an inlet-side, first measuring tube end 11# and an outlet-side, second measuring tube end 12# and is adapted to guide medium to be measured in its lumen and during that, not least of all for producing inertial forces dependent on density, to be caused to vibrate over its oscillatory length, in such a manner that the measuring tube 10 executes at least partially and/or at least at times wanted oscillations, namely mechanical oscillations, especially bending oscillations, about a resting position with a wanted frequency, $f_N$, especially a wanted frequency, $f_N$, co-determined by, respectively dependent on, density of the medium, along with a correspondingly repeated, elastic deformation of the tube wall. The oscillatory length corresponds in the example of an embodiment shown in FIG. 4, respectively 5, to a length measured from the measuring tube end 11# to the measuring tube end 12# of an imaginary central- or also centroidal, axis extending within the lumen, namely an imaginary connecting line through the centers of gravity of all cross sectional areas of the measuring tube, respectively—in the case of a curved measuring tube—to the arc length of the measuring tube 10. As directly evident from FIGS. 4 and 5, the at least one measuring tube 10 can be so formed that the aforementioned center line, such as quite usual in the case of measuring transducers of the type being discussed, lies in an imaginary tube plane of the measuring transducer.

In an embodiment of the invention, the wanted oscillations of the at least one measuring tube 10 are so embodied, consequently the at least one measuring tube 10 is so caused to vibrate during operation, that the measuring tube 10 executes over the entire oscillatory length oscillatory movements about an imaginary oscillation axis, which is parallel to or coincident with an imaginary connecting axis imaginarily connecting the two measuring tube ends 11#, 12#. The wanted oscillations can correspond, for example, to an oscillation form of a natural bending oscillation mode, for example, a bending oscillation fundamental mode, of the at least one measuring tube, consequently bending oscillations about the oscillation axis. The at least one measuring tube 10 can in advantageous manner, furthermore, be so formed and arranged in the measuring transducer that the aforementioned connecting axis, as a result, extends essentially parallel to an imaginary longitudinal axis L of the measuring transducer imaginarily connecting in—and outlet ends of the measuring transducer and, in given cases, also coinciding with the longitudinal axis L. Moreover, not least of all for the purpose of achieving a high mechanical durability, equally as well also for the purpose of achieving a high quality factor Q ($Q=f_R/B$) of greater than 1000 (Q>1000) at least for the bending oscillation fundamental mode of the at least one measuring tube 10 flowed-through by water, consequently a low bandwidth B ($B=f_R/Q$) of less than one hundredth of the instantaneous resonant frequency $f_R$ ($B<0.014 \cdot f_R$) of the bending oscillation fundamental mode—the at least one measuring tube 10 (manufactured, for example, of titanium, tantalum, respectively zirconium, or an alloy thereof, a nickel based alloy or a stainless steel) of the measuring transducer and, insofar, also an imaginary center line of the measuring tube 10 extending within the lumen can be embodied e.g. essentially U-shaped or, as well as also shown in FIGS. 4 and 5, essentially V-shaped. Since the measuring transducer MT should be applicable for a large number of different applications, especially in the field of industrial measuring- and automation technology, it is, furthermore, provided that the at least one measuring tube can have a caliber (inner diameter), which is greater than 1 mm, especially greater than 10 mm, at times, even greater than 80 mm. Particularly in the case of application of a measuring transducer manufactured in microsystem technology (MEMS), for example, namely with a measuring tube of silicon or titanium, the caliber of the at least one measuring tube can, as well as also mentioned in the above patents, U.S. Pat. No. B 6,477,901, U.S. Pat. No. B 6,647,778, respectively U.S. Pat. No. B 7,059,176, however, also be selected to be less than 1 mm, especially even less than 0.5 mm.

For the case shown in FIGS. 4 and 5, in which the inner part is formed by means of a single measuring tube, consequently except for the measuring tube 10 has no other measuring tube for guiding the medium, the inner part of the measuring transducer can, such as shown here, comprise, furthermore, a counteroscillator 20 mechanically coupled with the (single)—here curved—measuring tube 10, for example, also formed similarly to the measuring tube 10 with U-, respectively V, shape, for minimizing disturbing influences acting on the inner part, as well as also for reducing total oscillatory energy released by the respective measuring transducer to the connected process line. Said counteroscillator 20 is spaced laterally from the measuring tube 10 and affixed to the measuring tube 10 at a first coupling zone lastly defining the aforementioned first measuring tube end 11# on the inlet side and at a second coupling zone lastly defining the aforementioned second measuring tube end 12# on the outlet side. The counteroscillator 20—here extending essentially parallel to the measuring tube 10—is advantageously produced from a metal compatible with the measuring tube 10 as regards thermal expansion behavior, thus, a metal such as, for instance, steel, titanium, respectively zirconium. As shown in FIG. 2 or provided, among other things, also in the above mentioned U.S. Pat. No. B 7,360,451, the counteroscillator 20 can, for example, be formed by means of plates arranged to the left- and right sides of the measuring tube 10 or also (blind-) pipes to the left- and right sides of the measuring tube 10. Alternatively thereto, the counteroscillator 20 can—such as provided, for instance, in which U.S. Pat. No. B 6,666,098—also be formed by means of a single (blind-) tube extending laterally of the measuring tube and parallel thereto. As evident from a combination of FIGS. 4 and 5, the counteroscillator 20 in the example of an embodiment shown here is held by means of at least one, inlet-side, first coupler 31 on the first measuring tube end 11# and by means of at least one, outlet-side, second coupler 32 on the second measuring tube end 12#, especially a coupler 32 essentially identical to the coupler 31. Serving as couplers 31, 32, in such case, can be e.g. simple node plates, which are secured in corresponding manner on the inlet side and on the outlet side respectively to the measuring tube 10 and to the counteroscillator 20. Furthermore, —such as provided in the case of the example of an embodiment shown in FIGS. 4 and 5—a completely closed box or, in given cases, also a partially open frame formed by means of node plates spaced from one another in the direction of the imaginary longitudinal axis L of the measuring transducer together with protruding ends of the counteroscillator 20 on the inlet side and on the outlet side can serve as a coupler 31, respectively as a coupler 32.

As additionally evident from FIGS. 4 and 5, the measuring tube 10 in the example of an embodiment shown here is, furthermore, via a straight first connecting tube piece 11 opening on the inlet side in the region of the first coupling zone and via a straight second connecting tube piece 12, especially a straight second connecting tube piece 12 essentially identical to the first connecting tube piece 11, opening on the outlet side in the region of the second coupling zone, connected correspondingly to the process line supplying, respectively draining, the medium, wherein an inlet end of the inlet-side, connecting tube piece 11 forms for practical purposes the inlet end of the measuring transducer and an outlet end of the outlet-side, connecting tube piece 12 the outlet end of the measuring transducer. In advantageous manner, the measuring tube 10 and the two connecting tube pieces 11, 12 can be embodied as one piece, so that e.g. a single tubular stock, or semifinished part, of a material usual for such measuring transducers, such as e.g. stainless steel, titanium, zirconium, tantalum or corresponding alloys thereof, can serve for its manufacture. In the example of an embodiment shown in FIGS. 4 and 5, it is, furthermore, provided that the two connecting tube pieces 11, 12, are so oriented relative to one another as well as to the imaginary longitudinal axis L of the measuring transducer imaginarily connecting the two coupling zones that the inner part formed here by means of counteroscillator 20 and measuring tube 10 can, with twisting of the two connecting tube pieces 11, 12, move like a pendulum about the longitudinal axis L. For such purpose, the two connecting tube pieces 11, 12 are so oriented relative to one another that they extend essentially parallel to the imaginary longitudinal axis L, respectively the imaginary oscillation axis, respectively that the connecting tube pieces 11, 12 essentially align both with the longitudinal axis L as well as also with one another. Since the two connecting tube pieces 11, 12 in the example of an embodiment shown here are embodied, for practical purposes, essentially straight over their entire length, they are, accordingly, as a whole, oriented essentially aligned with one another as well as with the imaginary longitudinal axis L. The measuring transducer housing 100, which is bending- and torsionally stiff, especially in comparison with the measuring tube 10, is affixed, especially rigidly, to an inlet end of the inlet-side, connecting tube piece 11 distal relative to the first coupling zone as well as to a outlet end of the outlet-side, connecting tube piece 12 distal relative to the second coupling zone, in such a manner that the entire inner part—here formed by means of measuring tube 10 and counteroscillator 20—is not only completely encased by the measuring transducer housing 100, but also, as a result of its eigenmass and the spring action of the two connecting tube pieces 11, 12, is held oscillatably in the measuring transducer housing 100.

For the typical case, in which the measuring transducer MT is to be assembled releasably with the process line, for example, in the form of a metal pipeline, there are provided on the inlet side of the measuring transducer a first connecting flange 13 for connecting to a line segment of the process line supplying medium to the measuring transducer and on the outlet side a second connecting flange 14 for connecting to a line segment of the process line removing medium from the measuring transducer. The connecting flanges 13, 14 can, in such case, such as quite usual in the case of measuring transducers of the described type, also be integrated terminally in the measuring transducer housing 100, namely be embodied as an integral component of the measuring transducer housing. For example, the first connecting flange 13 can be arranged on the inlet-side, connecting tube piece 11 on its inlet end and the second connecting flange 14 on the outlet-side, connecting tube piece 12 on its outlet end by means of corresponding soldered-, brazed-, respectively welded, connections. For active exciting and maintaining of mechanical oscillations of the at least one measuring tube 10, not least of all also the wanted oscillations, the measuring device electronics ME includes, such as already mentioned, a driver circuit Exc and the measuring transducer MT at least one electromechanical oscillation exciter 41 electrically connected to the driver circuit Exc. The at least one oscillation exciter 41—here, a single oscillation exciter acting on the at least one measuring tube 10—can, for example, be so placed that, as well as also indicated in FIGS. 4 and 5 and such as quite usual in the case of measuring transducers of the type being discussed, it acts centrally on the measuring tube, namely in the region formed on the at least measuring tube 10 at the half oscillatory length. In an additional embodiment of the invention, it is provided that the at least one measuring tube 10 is excited actively during operation by means of the at least one oscillation exciter 41 at least at times to wanted oscillations, which are embodied predominantly or exclusively as bending oscillations about the imaginary oscillation axis. Especially, it is, in such case, furthermore, provided that the at least one measuring tube 10, such as quite usual in the case of such measuring transducers with curved measuring tube, is excited by means of the oscillation exciter 41 to such bending oscillations, in the case of which the at least one measuring tube 10 oscillating about the oscillation axis-, for instance, in the manner of a unilaterally clamped cantilever—bends at least partially according to an oscillation form of a natural bending oscillation, fundamental mode, in such a manner that the bending oscillations, consequently the wanted oscillations of the measuring tube have, in such case, only oscillation nodes in the region of the inlet-side, coupling zone defining the inlet-side, measuring tube end 11#, and in the region of the outlet-side, coupling zone defining the outlet-side, measuring tube end 12#.

In an additional embodiment of the invention, the oscillation exciter 41 is embodied as an electrodynamic oscillation exciter, namely constructed in the manner of a solenoid, in such a manner that the oscillation exciter 41 has an cylindrical exciter coil electrically connected to the driver circuit Exc, consequently to the measuring device electronics ME formed therewith, as well as a permanently magnetic armature, consequently an armature providing a magnetic field, and that the magnetic field interacts with an (alternating-) magnetic field generated in the exciter coil by means of the exciter signal in a manner effecting relative movements of armature and exciter coil. In the case of an inner part formed by means of counteroscillator and measuring tube, the exciter coil can be affixed, for example, on the counteroscillator 20 and the armature externally on the measuring tube 10. The oscillation exciter 41 can, however, for example, also be embodied as a piezoelectric oscillation exciter or also as an electrostatic oscillation exciter, namely one formed by means of a capacitor, of which a first capacitor plate can be affixed on the measuring tube and a second capacitor plate on the counteroscillator, or, such as quite usual not least of all in the case of measuring transducers formed by means of a measuring tube with very small caliber of less than 1 mm, on the respective measuring transducer housing.

For the mentioned case, in which the actively excited wanted oscillations are bending oscillations of the measuring tube, these can in the case of the measuring transducer corresponding to the example of an embodiment shown in FIGS. 4 and 5, namely having an inner part formed by means of measuring tube 10 and counteroscillator 20, be so embodied in advantageous manner that the measuring tube 10 executes oscillatory movements, which periodically change a relative separation between measuring tube 10 and counteroscillator 20 with a wanted frequency $f_N$. In the case of an oscillation exciter acting simultaneously, for example, differentially, both on measuring tube as well as also on counteroscillator, in such case, also the counteroscillator 20 can be excited to execute simultaneous cantilever oscillations, for example, also in such a manner that it executes oscillations of frequency equal to that of the wanted oscillations, for example, bending oscillations about an imaginary oscillation axis parallel to the longitudinal axis L, which at least partially, namely especially in the region of the point of engagement formed by means of the oscillation exciter 41, and/or at least at times, namely at times when medium is not flowing through measuring tube, are essentially of opposite phase to those of the measuring tube 10. The oscillations of the counteroscillator 20 can, in such case, be so embodied that they are of equal modal order as the wanted oscillations. In other words, measuring tube 10 and counteroscillator 20 can then move in the manner of tuning fork tines oscillating opposite to one another.

The driver circuit Exc, consequently the measuring device electronics of the density measuring device of the invention formed therewith, is, furthermore, adapted to generate an (analog) electrical exciter signal $e_1$ and by means of the exciter signal $e_1$ to supply electrical power $E_{exc}$ to the oscillation exciter 41. The exciter signal $e_1$ can, such as quite usual in the case of the density measuring devices of the type being discussed, be an at least at times an harmonic electrical alternating signal having an impressed alternating voltage and/or an impressed alternating electrical current. For setting the exciter signal to a signal frequency corresponding to the wanted frequency to be excited, a digital phase locked loop (PLL) can, for example, be provided in the driver circuit, while an electrical current level of the exciter signal determinative of the magnitude of the exciter forces can be suitably set, for example, by means of a corresponding, in given cases, digital, electrical current controller of the driver circuit. The practical construction and application of such phase locked loops for the active exciting of measuring tubes to a predetermined wanted frequency is known, per se, to those skilled in the art. The generating of the exciter signal $e_1$ can, for example, also occur based on a digital control signal $e_{1D}$, which is firstly generated by means of the measuring- and evaluating circuit μC and by means of which during operation, for example, a power amplifier contained in the driver circuit Exc and lastly providing the exciter signal $e_1$ is operated. The digital control signal $e_{1D}$ can be a digital signal, for example, even a sinusoidal digital signal, generated, for example, by means of a numerically controlled oscillator (NCO). The measuring device electronics ME can e.g. additionally also be embodied to control the exciter signal in such a manner that the wanted oscillations have a constant amplitude, consequently also largely independent of density ρ, respectively also viscosity η, of the respective medium to be measured. Of course, also other driver circuits suitable for setting the electrical excitation power, respectively the appropriate signal frequency of the exciter signal, and known to those skilled in the art, per se, for example, also from the above mentioned U.S. Pat. No. A 4,801,897, U.S. Pat. No. A 5,024,104, respectively U.S. Pat. No. A 6,311,136, can be used for implementation of the density measuring device of the invention. The oscillation exciter 41, in turn, serves, respectively is adapted, to convert electrical power $E_{exc}$ fed by means of the exciter signal e1 into a drive force F, consequently a force dependent on the supplied electrical power $E_{exc}$, acting on a (force-) point of engagement on the at least one measuring tube formed by means of the oscillation exciter 41 and deflecting the measuring tube in the above-described manner, respectively exciting oscillations of the at least one measuring tube, wherein the (naturally vectorial) drive force F is so formed for the purpose of a targeted exciting of the wanted oscillations that it introduces a wanted force component $F_N$ into the at least one measuring tube 10, namely a periodic force component changing with an excitation frequency corresponding to the wanted frequency $f_N$ and ultimately effecting the wanted oscillations. In supplementation as regards construction and operation of such driver circuits suitable for the density measuring device of the invention, reference is made to the measuring device electronics provided with measurement transmitters of the series "PROMASS 83F", such as sold by the applicant, for example, in connection with measuring transducers of the series "PROMASS F". Their driver circuit is, for example, in each case, also so executed that the respective wanted oscillations are controlled to a constant amplitude, thus an amplitude also largely independent of density ρ, respectively viscosity η.

For registering oscillations of the measuring tube 10, not least of all also the excited, wanted oscillations, respectively the velocity response corresponding therewith, the measuring transducer further comprises a first oscillation sensor 51, for example, electrically connected to the measuring device electronics ME by means of an additional pair of connection wires (not shown). The oscillation sensor 51, in such case, is adapted to register oscillatory movements of the at least one measuring tube—not least of all oscillatory movements corresponding to the wanted oscillations, respectively movements of oscillations of the measuring tube with the wanted frequency $f_N$—and to transduce such into a first oscillation measurement signal Si representing these and serving as a primary signal of the measuring transducer and having, for example, a voltage corresponding to a velocity of the registered oscillatory movements or an electrical current corresponding to the registered oscillatory movements. Because the at least one measuring tube 10 executes the mentioned wanted oscillations, consequently oscillations with the wanted frequency, the oscillation measurement signal $s_1$ generated by means of the oscillation sensor 51 has a signal frequency corresponding to the wanted frequency, respectively the oscillation measurement signal $s_1$ contains—for instance, in the case of a broadband and/or multimodal oscillation excitement by disturbances entering externally via the connected pipeline and/or via the through-flowing medium—at least a corresponding wanted signal component, namely a periodic signal component having a signal frequency corresponding to the wanted frequency $f_N$. The oscillation sensor 51 can be embodied, for example, as an electrodynamic oscillation sensor, namely one constructed in the manner of a solenoid, in such a manner that the oscillation sensor 51 has a cylindrical sensor coil held on the counteroscillator 20 and at the same time electrically connected to the measuring- and evaluating circuit, consequently to the measuring device electronics ME formed therewith, as well as a permanently magnetic armature, consequently an armature containing a magnetic field, affixed outwardly on the measuring tube 10, for example, connected with its tube wall by material bonding, and that the magnetic field, as a result of a relative movement of armature and sensor coil related to the oscillatory movements of the measuring tube, induces in the sensor coil an (alternating) voltage serviceable as an oscillation measurement signal. The oscillation sensor 51 can, however, for example, also be embodied as a capacitive oscillation sensor formed by means of a capacitor, of which a first capacitor plate can be affixed to the measuring tube and a second capacitor plate to the counteroscillator.

In an additional embodiment of the invention, not least of all also for the already mentioned case, in which the density measuring device supplementally is also helpful for measuring a mass flow rate, respectively a mass flow, the oscillation sensor 51 is arranged spaced from the oscillation exciter 41 along the at least measuring tube, for example, in such a manner that therewith inlet-side, oscillatory movements of the measuring tube, namely-, as well as also shown schematically in FIG. 3—oscillatory movements of the at least one measuring tube 10 can be registered at a measuring point located between the measuring tube end #11 and the oscillation exciter 51 and spaced from both the measuring tube end #11 and the oscillation exciter 51.

The oscillation measurement signal Si generated by means of the oscillation sensor 51 is, as well as also shown in FIG. 3, fed to the measuring device electronics ME and there firstly to an input circuit FE, which serves, firstly, suitably to preprocess the oscillation measurement signal $s_1$, namely to condition such appropriately for a digital signal processing underlying the actual density measurement, for example, namely to pre-amplify, to filter and to digitize the oscillation measurement signal Applied as input circuit FE as well as also measuring- and evaluating circuit μC can be circuit technologies already applied and established in such case also in conventional density-, respectively Coriolis mass flow-/density, measuring devices for the purpose of converting primary signals delivered by means of a measuring transducer of vibration-type, respectively for the purpose of ascertaining measured values representing density, in given cases, also the mass flow rate and/or the viscosity, for example, also circuit technologies according to the above cited state of the art. Particularly for the mentioned case, in which the measuring- and evaluating circuit μC, such as, among other things, also shown in the above cited U.S. Pat. No. 6,311,136 or also implemented in the aforementioned measurement transmitters of the measuring device series "PROMASS 83F", is formed by means of at least one microprocessor, consequently is provided for processing digital signals, the measuring device electronics is, furthermore, adapted to convert the oscillation signal $s_1$ by means of an analog-to-digital converter A/D into a corresponding digital oscillation measurement signal $s_{1D}$ and thereafter to process such further, respectively to evaluate such, digitally.

As already mentioned, the measuring device electronics of the density measuring device of the invention is, especially, adapted, with application of the oscillation measurement signal $s_1$, for example, also a digital oscillation measurement signal $s_{1D}$ won therefrom, to generate, respectively recurringly to update, a density measured value $X_\rho$ instantaneously representing density of the medium guided in the measuring transducer. The ascertaining of the density measured value $X_\rho$ can, in such case, e.g. occur taking into consideration a known relationship—not least of all also used in conventional density measuring devices for measuring density—as follows $$f_N^2 = \frac{B}{\rho - A}, \tag{1}$$

consequently that with application of the at least one oscillation measurement signal $s_1$ firstly the instantaneous wanted frequency $f_N$ is ascertained and thereafter said instantaneous wanted frequency $f_N$ is converted into the density measured value $X_\rho$ instantaneously representing density; this, for example, in such a manner that the density measured value $X_\rho$ at least approximately and/or at least for the case, in which the medium to be measured has a temperature corresponding to a reference temperature, fulfills the condition $$X_\rho = A + \frac{B}{f_N^2}. \tag{2}$$

Therefore, the measuring- and evaluating circuit, consequently the measuring device electronics ME formed therewith, of the density measuring device of the invention is, furthermore, among other things, also adapted to ascertain, respectively recurringly to update, during operation, a frequency measured value $X_f$ representing the wanted frequency $f_N$, for example, with application of the exciter signal of and/or the at least one oscillation measurement signal $s_1$, as well as to use the frequency measured value $X_f$ for ascertaining a density measured value $X_\rho$, respectively density measured values. For example, the density measured value $X_\rho$, respectively density measured values, can be calculated by means of the measuring- and evaluating circuit based on a calculational specification appropriately derived from the previously indicated condition:

$$X_\rho = A + \frac{B}{X_f^2}. \qquad (3)$$

The measuring-device-specific coefficients A and B appearing in the calculational specification can, in turn, be ascertained earlier in manner known, per se, to those skilled in the art by calibrating the density measuring device with different media with different densities, for example, air, respectively water and/or glycerin, for example, also, in each case, held at a temperature corresponding to the mentioned reference temperature, for example, in the course of a wet calibration performed in the manufacturer's plant.

Figure 7:
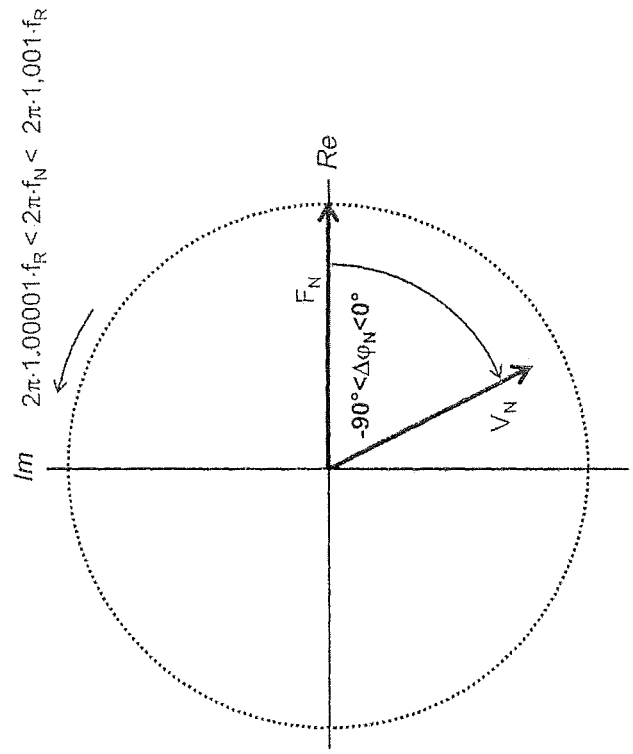
FIGS. 6 and 7 are phasor diagrams illustrating oscillatory movements of a measuring tube of a measuring transducer according to FIGS. 4 and 5.
Figure 6:
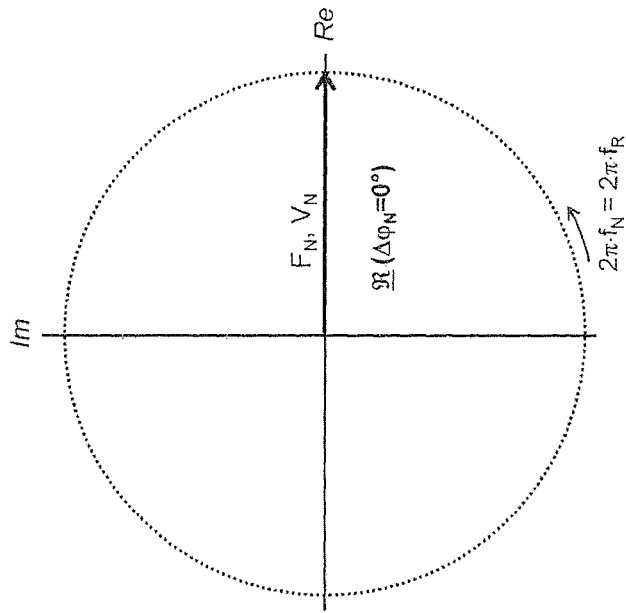

In The wanted oscillations of the at least one measuring tube 10 resulting from its natural oscillation characteristics and excited for ascertaining the density are so developed that—such as illustrated in FIG. 6, respectively 7, by means of a so-called phasor model or also phasor diagram—a velocity response $V_N$ of the at least one measuring morning tube 10, namely a velocity of the oscillatory movements of the at least one measuring tube 10 at the point of engagement changing with the wanted frequency $f_N$ as a function of time, is phase shifted from the wanted force component $F_N$ of the drive force by a certain phase shift angle $\varphi_N$, which depends on the actually set excitation frequency, consequently on the actually set wanted frequency $f_N$. Due to the natural oscillation characteristics naturally inherent to the measuring tube 10, respectively the inner part formed therewith, respectively the dynamic transfer behavior of the measuring transducer resulting therefrom, the above mentioned dependence of the velocity response $V_N$ on the wanted force component $F_N$ is such that, for the case, in which the set excitation frequency—such as usual in the case of conventional density measuring devices of the type being discussed—corresponds to an instantaneous resonant frequency of the at least one measuring tube 10, consequently the resonance condition ($\Re$) is fulfilled, the phase shift angle $\varphi_N$ is approximately zero (FIG. 6), and that for the case, in which the resonance condition ($\Re$) is not fulfilled, for example, in that the set wanted frequency $f_N$ is greater than 1.00001 times, equally as well less than 1.001 times, an instantaneous resonant frequency of the at least one measuring tube 10, moreover, however, also corresponds to no other resonant frequency of the at least one measuring tube, the phase shift angle $\varphi_N$ amounts to less than 0°, for example, namely, for instance, −50° to −70° (FIG. 7). In the case of application of a measuring tube manufactured of stainless steel with a caliber of 29 mm, a wall thickness, for instance, of 1.5 mm, an oscillatory length of, for instance, 420 mm and a chordal length, measured as the shortest separation of the two measuring tube ends #11, #12, of 305 mm, a resonant frequency of the at least one measuring tube corresponding to the bending oscillation fundamental mode would, for the case, in which such is filled only with air, consequently density ρ of the medium is, for example, practically zero, be, for instance, 490 Hz. Accordingly, for such a configuration of the measuring transducer, the excitation-, respectively the wanted, frequency at a phase shift angle $\varphi_N$ amounting to between −50° to −70° can lie, for instance, between 490.05 Hz and 490.5 Hz. The drive force F, in turn, respectively its wanted force component $F_N$, can, in manner known, per se, to those skilled in the art, be adjusted precisely as regards its amplitude e.g. by means of a correspondingly conditioned, electrical current level, respectively voltage level, of the electrical exciter signal e1, respectively as regards its excitation frequency by setting a signal frequency of the exciter signal $e_1$. Accordingly, the measuring device electronics is according to an additional embodiment of the invention adapted to adjust the drive force F, not least of all namely its wanted force component $F_N$, by changing a signal frequency of the exciter signal $e_1$. For example, for the above-described case, in which a sinusoidal digital signal serves as digital control signal $e_{1D}$ for the driver circuit, also the control signal $e_{1D}$—, in given cases, taking into consideration an actual transfer behavior of the driver circuit Exc and/or of the at least one oscillation exciter 41—can be set as regards both frequency as well as also amplitude by means of the measuring- and evaluating circuit μC already suitably to the desired wanted force component.

Characteristic for the wanted frequency $f_N$ respectively applied in the case of density measuring devices of the type being discussed for measuring density ρ is that it regularly concerns an oscillation frequency, in the case of which the phase shift angle $\varphi_N$ between the velocity response $V_N$ and the wanted force component $F_N$ of the drive force F is set to a correspondingly predetermined desired phase value, respectively, conversely, to a correspondingly predetermined desired phase value, which results, after the phase shift angle $\varphi_N$ has been controlled, for instance, through continuous or virtually continuous, respectively step-wise modifying of the excitation frequency, by means of the measuring device electronics, at least to a predetermined phase control interval, namely locked to the respective desired phase value required for the actual measuring of the wanted frequency.

In conventional density measuring devices, such as already mentioned, there typically serve as resonant oscillations, consequently such oscillations serve as a wanted oscillation, in the case of which the phase shift angle $\varphi_N$ amounts at least approximately to 0°, respectively ideally is exactly zero, in the case of which thus the above mentioned resonance condition ($\Re$) is fulfilled (compare FIG. 6). The actual duration of the respectively required phase control interval is determined, on the one hand, not least of all by a dynamic range, namely behavior as a function of time, of the mechatronic system formed by means of the oscillation exciter, the at least one measuring tube, the at least one oscillation sensor as well as the measuring device electronics, especially the measuring- and evaluating circuit and the driver circuit, as a whole, as well as by a processing speed, respectively updating rate, with which the measuring- and evaluating circuit can ascertain the wanted frequency based on the oscillation signal and generate the corresponding frequency measured values. In the case of the density measuring devices of the type being discussed, the updating rates for the frequency measured values lie typically in the range of, for instance, 100 Hz to, for instance, 200 Hz.

Accordingly, the measuring device electronics ME of the density measuring device of the invention is, furthermore, adapted by means of the oscillation measurement signal $s_1$ and the exciter signal $e_1$ to adjust the drive force required for the active exciting of the wanted oscillations in such a manner that during a predetermined phase control interval $\Delta t_\varphi$ of, for example, 10 ms or longer, the phase shift angle $\varphi_N$ is set to a predetermined desired phase value $\varphi_{N\_DES}$. An actual required duration of the phase control interval $\Delta t_\varphi$ (naturally visited repeatedly by the measuring device electronics during operation) depends, on the one hand, on a speed with which the wanted frequency of a time changing density can be suitably adjusted during operation and, on the other hand, among other things, also, on how many oscillation periods of the wanted oscillations should actually be registered, in each case, for an individual frequency measured value, respectively how many oscillation periods of the oscillation measurement signal should, in each case, actually be evaluated.

In an additional embodiment of the invention, the measuring device electronics is adapted, furthermore, to bring the phase shift angle $\varphi_N$ to a predetermined desired phase value $\varphi_{N\_DES}$, namely to set such to a corresponding phase value, respectively to hold such at a corresponding phase value, in such a manner that the phase shift angle $\varphi_N$ in the case of constant density fluctuates by less than ±1% of the desired phase value $\varphi_{N\_DES}$ and/or by less than ±2° around the desired phase value $\varphi_{N\_DES}$, respectively ideally during the total phase control interval and/or in the case of instantaneously non-varying density $\rho$ is held constant, consequently stationary, at the desired phase value $\varphi_{N\_DES}$.

The controlling of the phase shift angle $\varphi_N$ to the desired phase value $\varphi_{N\_DES}$ can occur by changing a signal frequency of the exciter signal e1 until the phase shift angle $\varphi_N$ has achieved a predetermined desired phase value $\varphi_{N\_DES}$, for example, namely in such a manner that the measuring device electronics in the case of a phase shift angle $\varphi_N$ set too small, namely less than the desired phase value $\varphi_{N\_DES}$, lessens the signal frequency, and in such a manner that the measuring device electronics in the case of a phase shift angle $\varphi_N$ set too large, namely greater than the desired phase value $\varphi_{N\_DES}$, increases the signal frequency. A phase value for the instantaneously actually set phase shift angle $\varphi_N$ can, in turn, come from the measuring- and evaluating circuit µC, for example, based on a phase angle ascertained between the oscillation measurement signal $s_1$ and the exciter signal $e_1$ and regularly present in any event during operation in measuring device electronics of the density measuring devices of the type being discussed.

The desired phase value $\varphi_{N\_DES}$ can in case required-, for instance, for the purpose of measuring still other measured variables, such as e.g. viscosity η, of the medium guided in the at least one measuring tube 10—also be changeable, in such a manner that the measuring device electronics replaces the desired phase value $\varphi_{N\_DES}$ predetermined for measuring density temporarily with another desired phase value correspondingly predetermined for an additional device function differing from the measuring of density, in such a manner that the measuring device electronics thereafter locks the phase shift angle $\varphi_N$ at the desired phase value.

Figure 8:
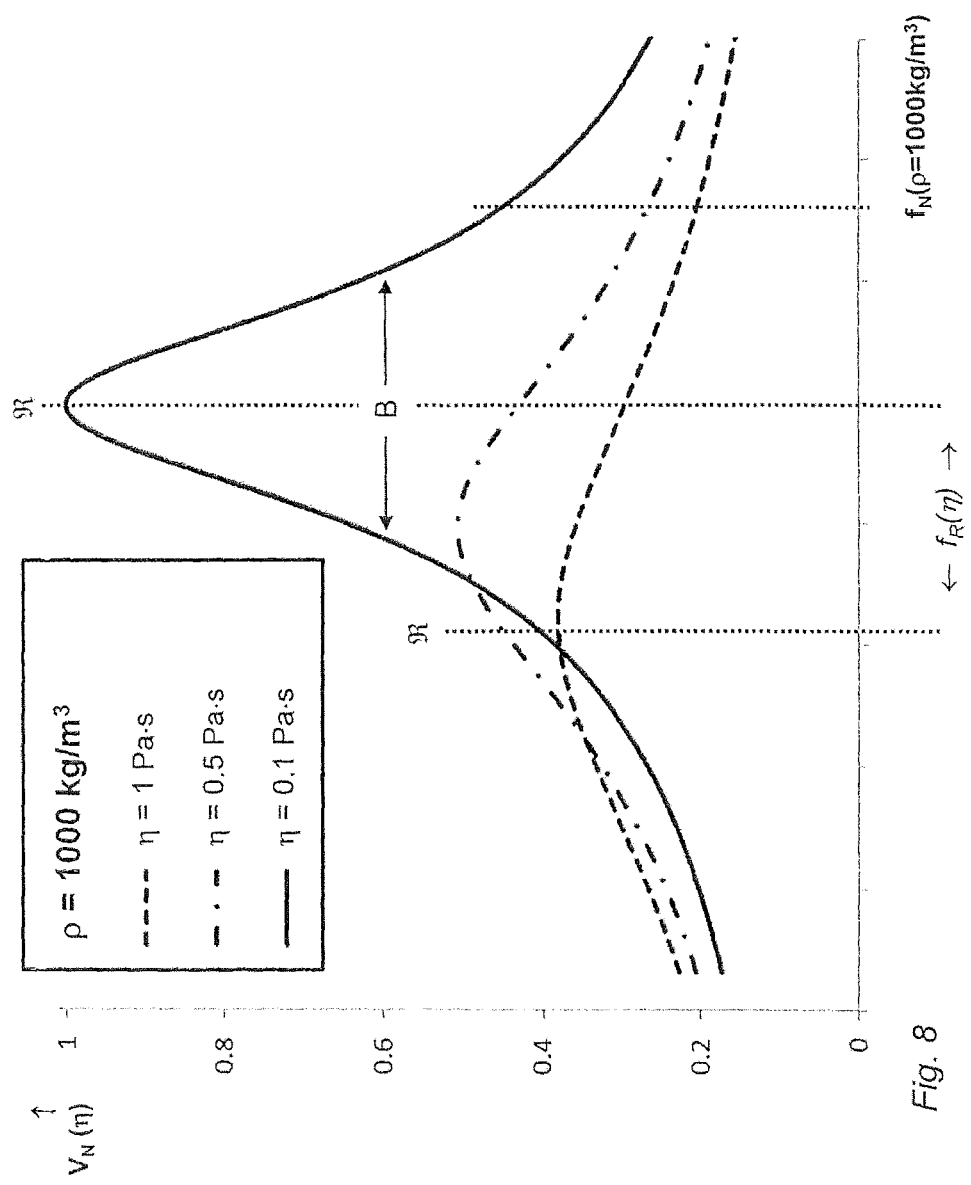
FIGS. 8 and 9 are oscillatory movements of a measuring tube of a measuring transducer according to FIGS. 4 and 5 illustrating amplitude frequency responses as a function of density and/or viscosity of a medium guided in the measuring tube.
Figure 9:
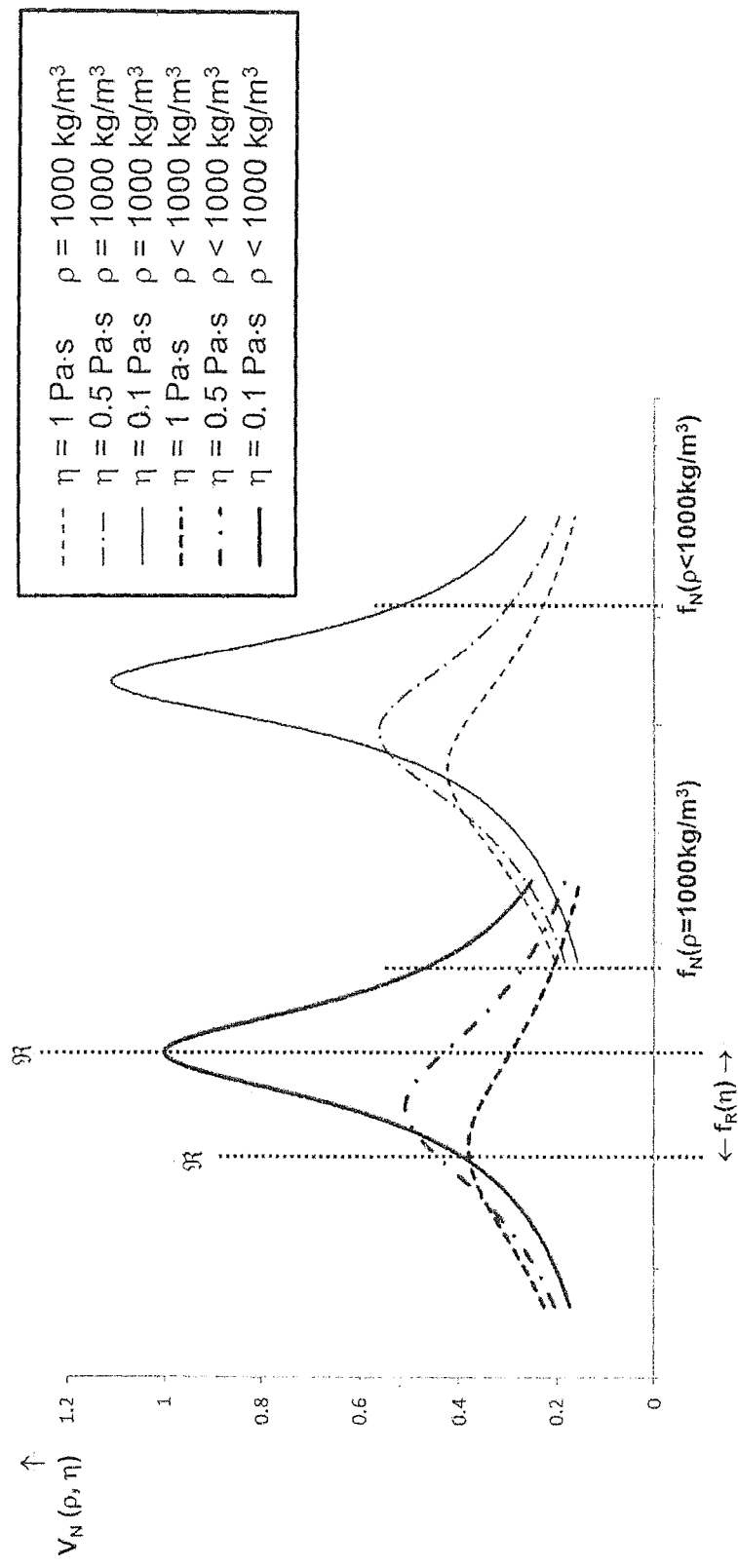

In the case of the density measuring device of the invention, the wanted oscillations are—in contrast to the case for conventional density measuring devices—so embodied that the phase shift angle $\varphi_N$ for the purpose of measuring the wanted frequency $f_N$ required for ascertaining density is set by means of the measuring device electronics to less than −20° and greater than −80°, respectively, conversely, that the wanted frequency $f_N$ is so set by means of the measuring device electronics that the wanted frequency $f_N$ is greater than 1.00001 times, equally as well less than 1.001 times a resonant frequency $f_R$ of the at least one measuring tube, moreover, however, also corresponds to no other resonant frequency of the at least one measuring tube 10, consequently the ascertaining of density occurs at wanted oscillations, at which the resonance condition ($\Re$) is namely not fulfilled. By applying wanted oscillations having such a phase shift angle $\varphi_N$, respectively such a wanted frequency $f_N$, namely a dependence (shown in FIG. 8, respectively 9, based on graphs illustrating dependence of the velocity response $V_N$ on the selected excitation frequency (amplitude frequency response), respectively in FIG. 10 based on a graph illustrating dependence of the wanted frequency $f_N$ on the selected phase shift angle $\varphi_N$ (phase frequency response)) of the excitation-, respectively wanted frequency $f_N$ (corresponding to the phase shift angle $\varphi_N$ to be adjusted, respectively set) also on an instantaneous viscosity η of the medium, resulting from a dependence of the phase shift angle $\varphi_N$ (set corresponding to the desired phase value) on an instantaneous damping counteracting the excited wanted oscillations, can be almost eliminated, at least, however, in considerable measure reduced. As additionally directly evident from FIG. 10, the dependence of the phase shift angle $\varphi_N$ on the instantaneous, equally as well time variable, damping is especially strong in the region of the resonant frequency $f_R$ preferably used in conventional density measuring devices of the type being discussed for measuring density, while the dependence at smaller, namely negative, phase shift angles $\varphi_N$, consequently at excitation-, respectively wanted, frequencies $f_N$ lying in the frequency range slightly above the resonant frequency $f_R$ decreases, respectively practically is no longer measurable. Conversely, such as evident, furthermore, from the combination of FIGS. 8, 9 and 10, especially the resonant frequency $f_R$ (not least of all also hitherto (exclusively) applied as wanted frequency in conventional density measuring devices for ascertaining density) can also have for the high accuracy of measurement desired for density measuring devices of the type being discussed regularly a quite considerable dependence also on the damping of the wanted oscillations, respectively the viscosity η of the respective medium causing the damping.

Figure 10:
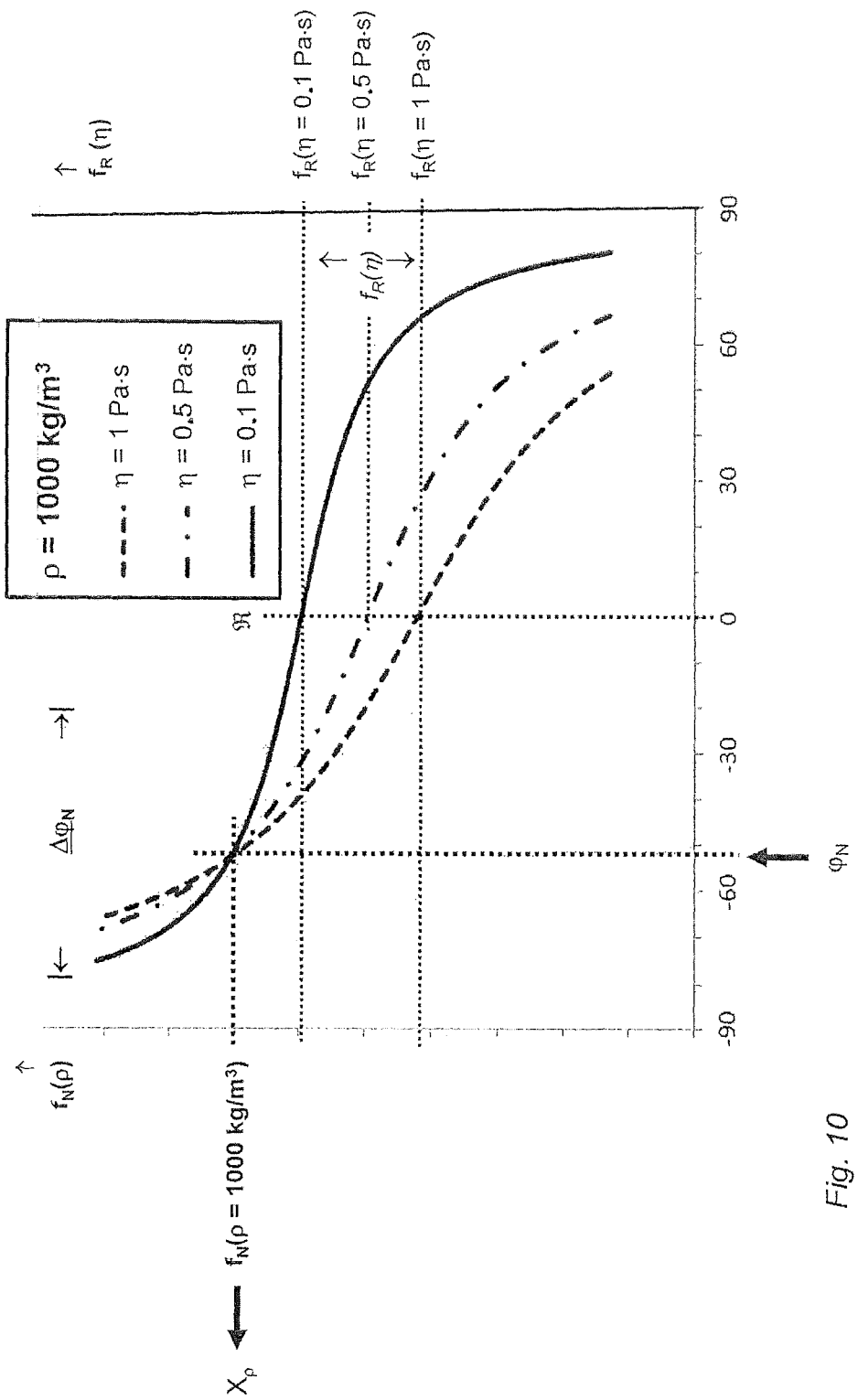
FIGS. 10 and 11 are oscillatory movements of a measuring tube of a measuring transducer according to FIGS. 4 and 5 illustrating phase frequency responses as a function of density and/or viscosity of a medium guided in the measuring tube.
Figure 11:
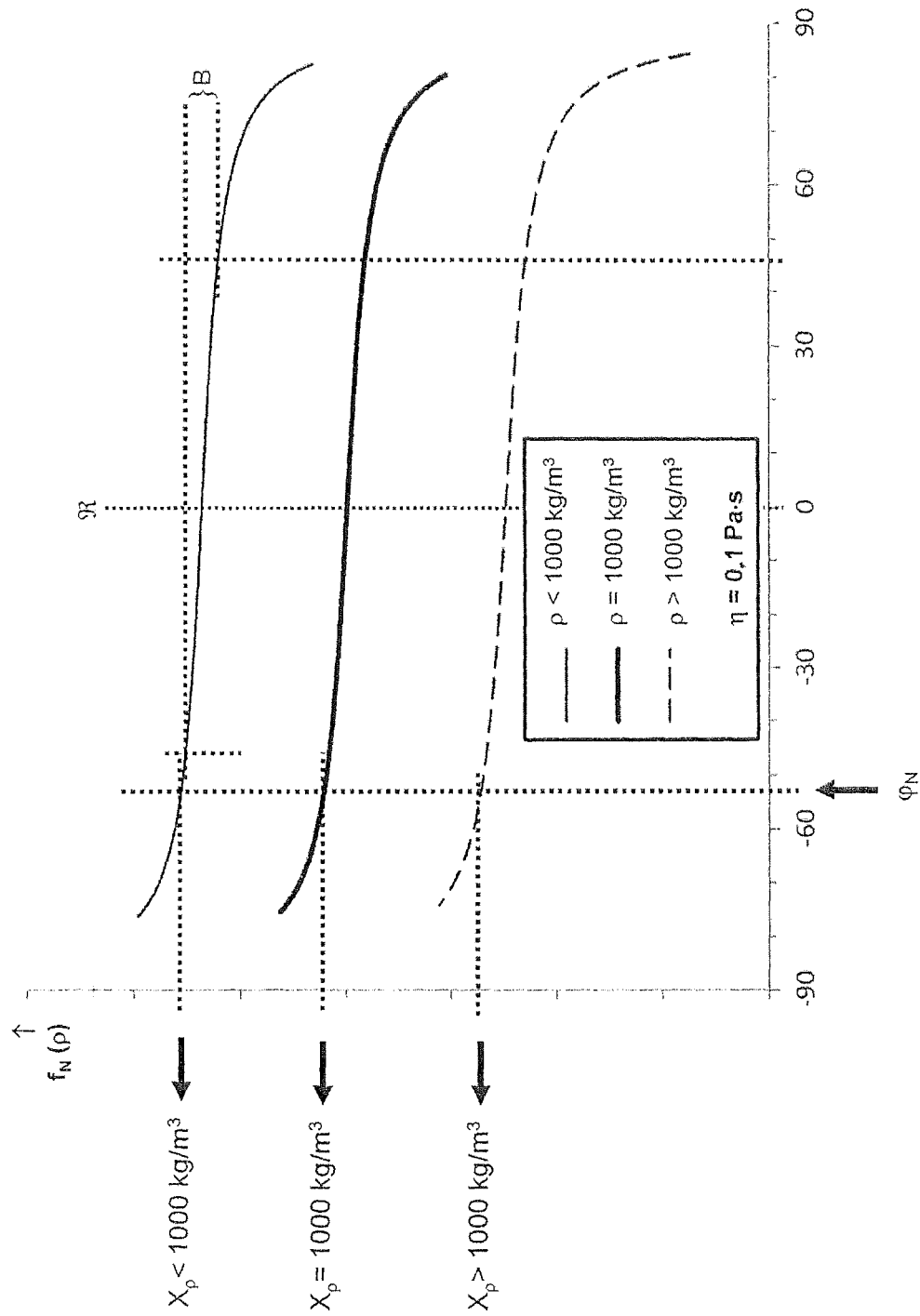

For lessening the above indicated dependence of the phase shift angle $\varphi_N$ on the instantaneous damping opposing the excited wanted oscillations, the measuring device electronics of the density measuring device of the invention is accordingly, furthermore, adapted, by means of the oscillation measurement signal $s_1$ as well as the exciter signal $e_1$ so to adjust the drive force, especially namely the wanted force component, respectively its excitation frequency, that the phase shift angle $\varphi_N$, as well as also shown in FIG. 10, by way of example, based on phase frequency responses of the measuring transducer ascertained for 3 mutually differing densities, is during the phase control interval $\Delta t_\varphi$ less than −20° and greater than −80°, especially namely less than −30° and/or greater than −70°, consequently the wanted frequency during the phase control interval $\Delta t_\varphi$ has a frequency value, which is greater than 1.00001 times, equally as well less than 1.001 times, an instantaneous frequency value of a resonant frequency $f_R$ of the at least one measuring tube 10. Moreover, the measuring device electronics is adapted, based on the oscillation measurement signal s1 won during the phase control interval, to ascertain the at least one frequency measured value $X_f$, in such a manner that the frequency measured value $X_f$ represents the wanted frequency for the phase control interval $\Delta t_\varphi$, as well as to generate the density measured value $X_\rho$ using the frequency measured value $X_f$.

A phase shift angle $\varphi_N$ suitable for the respective measuring transducer, respectively the density measuring device formed therewith, can be ascertained earlier, for example, by computer supported simulation and/or experimentally, for example, by ascertaining, such as, among other things, also from FIG. 10 evident, for two or more reference media with viscosities different from one another, equally as well at least approximately equal density, respectively associated frequency responses, and based on the frequency responses, for instance, by ascertaining an intersection of a number of frequency responses, respectively an average intersection formed by a number of such neighboring intersections, establishing as desired phase value $\varphi_{N\_DES}$ a phase value, for instance, −52° as shown in the graph in FIG. 10, having a minimum dependence on viscosity.

Accordingly, the measuring device electronics according to an additional embodiment of the invention is, furthermore, also adapted to keep a signal frequency of the exciter signal $e_1$ during the total phase control interval at a frequency value, which amounts to not less than 1.0001 times a resonant frequency $f_R$ of the at least one measuring tube, for example, namely a lowest resonant frequency and/or a resonant frequency corresponding to a bending oscillation fundamental mode, and no greater than 1.01 times the resonant frequency. The setting of the frequency of the exciter signal, consequently the wanted frequency $f_N$, can occur, such as quite usual in the case of the density measuring devices of the type being discussed, with application of a digital phase locked loop (PLL) provided in the measuring device electronics and implemented, for example, by means of the measuring- and evaluating circuit µC, wherein the phase locked loop (PLL) utilizes the previously indicated relationship between instantaneous excitation-, respectively wanted, frequency $f_N$ and instantaneous phase shift angle $\varphi_N$ for conforming the control signal $e_{1D}$ to the instantaneous oscillation characteristics of the inner part formed by means of the at least one measuring tube 10. The controlling of the phase shift angle $\varphi_N$ to the desired phase value $\varphi_{N\_DES}$ can occur, for example, by having the phase locked loop change a signal frequency of the exciter signal e1 until the phase locked loop, based on the mentioned oscillation measurement signal $s_1$, respectively with application of a digital auxiliary signal won therefrom, such as e.g. the mentioned digital oscillation measurement signal $s_{1D}$, detects an agreement of phase shift angle $\varphi_N$ and predetermined desired phase value $\varphi_{N\_DES}$, respectively by having the phase locked loop not change the signal frequency of the exciter signal e1, once agreement of the phase shift angle $\varphi_N$ with the desired phase value $\varphi_{N\_DES}$ is detected.

Figure 12:
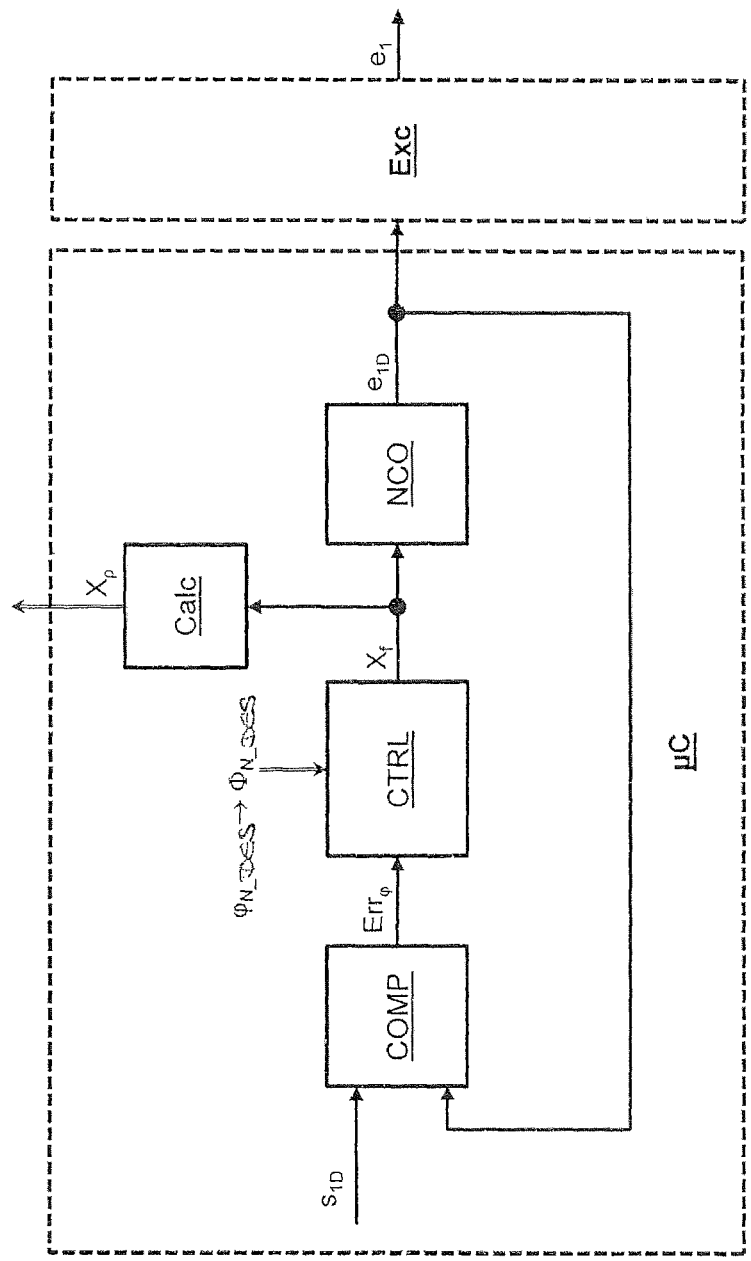
FIG. 12 shows schematically in the manner of a type of block diagram, an example of an embodiment of a phase locked loop (PLL) suitable for a density measuring device according to FIGS. 1 and 2.

Construction and operation of such phase locked loops, not least of all, however, also their application in vibronic density measuring devices for the active exciting of wanted oscillations, respectively for adjusting a wanted frequency, are known, per se, to those skilled in the art. As shown schematically in FIG. 12, a digital phase locked loop suitable for application in a density measuring device of the invention for controlling the excitation frequency, consequently the wanted frequency $f_N$, can have a phase comparator COMP, by means of which recurringly a comparison of an instantaneous phase position of the digital oscillation measurement signal $s_{1D}$ lying on a first input with an instantaneous phase position of the control signal $e_{1D}$—here formed as a sinusoidal digital signal—fed back to a second input is performed and by means of which, based on the comparison, an error signal $Err_\varphi$ is generated, which signals whether, respectively to what extent, the phase positions of the signals lying on the two inputs—here namely the digital oscillation measurement signal $s_{1D}$ and the digital control signal $e_{1D}$—differ from one another. The error signal $Err_\varphi$ is then fed to a frequency controller CTRL, which serves, taking into consideration a phase control desired value $\Phi_{N\_DES}$ previously given to the frequency controller CTRL, for example, fixedly programmed in, to convert the error signal $Err_\varphi$ into an numerical control value available on an output of the frequency controller CTRL and representing a signal frequency for the instantaneously output control signal $e_{1D}$. Said phase control desired value $\Phi_{N\_DES}$ corresponds to a numerical phase value, which is ascertained earlier based on the phase value $\varphi_{N\_DES}$ actually desired for the phase shift angle $\varphi_N$, and, indeed, also taking into consideration possible further influences effected by the density measuring device—for example, namely by the oscillation exciter, the at least one oscillation sensor and/or the measuring device electronics, especially its measuring- and evaluating circuit, respectively its driver circuit, —on a phase shift between the exciter signal $e_1$ and the at least one oscillation measurement signal $s_1$. For example, construction and operation of the oscillation exciter is correspondingly to be taken into consideration in the calculating of the phase control desired value $\Phi_{N\_DES}$, not least of all also in such a manner that for the mentioned case, for instance, that the oscillation exciter 41 is embodied in the manner of a type of solenoid, the wanted excitation component of the exciter signal $e_1$ has a periodic electrical current at least approximately frequency- and at least approximately phase equal with the wanted force component $F_N$, equally as well a periodic voltage, indeed, of frequency equal to that of the wanted force component $F_N$, however, phase-shifted by an order of magnitude of 90°, or for the other case, in which the oscillation exciter is of electrostatic type, namely formed by means of a capacitor, an electrical voltage of the exciter signal $e_1$ has a periodic voltage component at least approximately frequency- and phase equal with the wanted force component $F_N$, equally as well a periodic electrical current, indeed, of frequency equal to that of the wanted force component $F_N$, however, phase-shifted by an order of magnitude of 90°. Equally to be taken into consideration in calculating the phase control desired value $\Phi_{N\_DES}$ are, among other things, also construction and operation of the at least one oscillation sensor 51. For the mentioned case, in which the at least one oscillation sensor 51 is embodied in the manner of a type of solenoid, the oscillation measurement signal $s_1$ has a periodic voltage with a frequency- and at least approximately equal phase of the velocity response $V_N$ of the at least one measuring tube, while, for example, the oscillation measurement signal $s_1$ has for the other mentioned case, in which the oscillation sensor is formed by means of a capacitor, a frequency equal to that of the velocity response of the at least one measuring tube, equally as well a periodic electrical current phase-shifted relative to the velocity response by, for instance, +90°. Furthermore, the signal transfer behavior of the measuring device electronics, not least of all as also determined by the interaction of the driver circuit and the oscillation exciter, respectively the oscillation sensor and the input circuit FE, not least of all also a phase frequency response of the measuring device electronics resulting therefrom, is to be correspondingly included in the calculating of the phase control desired value $\Phi_{N\_DES}$, respectively group travel times naturally inherent to the measuring device electronics, not least of all to the mentioned input circuit, to the measuring- and evaluating circuit as well as also to the driver circuit, along with additional phase shifts, namely travel time related phase shifts, for instance, of the mentioned digital oscillation measurement signal $s_{1D}$ relative to the oscillation measurement signal $s_1$ or also of the exciter signal e1 relative to the mentioned digital control signal en) are correspondingly to be calculated into the phase control desired value $\Phi_{N\_DES}$. The phase control desired value $\varphi_{N\_DES}$ actually suitable for the density measuring device can, for example, be experimentally measured in the course of a calibration of the density measuring device performed in the manufacturer's plant and thereafter stored in the mentioned non-volatile memory EEPROM of the measuring device electronics. The above mentioned control value output of the frequency controller CTRL representing the signal frequency is, furthermore, transferred to an oscillator, here a numerically controlled oscillator NCO, which delivers on an output the digital control signal $e_{1D}$, which is supplied to the driver circuit and has a signal frequency determined by the instantaneous control value. By means of the so formed phase locked loop, the signal frequency and, as a result, the corresponding wanted frequency $f_N$ can be held at the frequency value corresponding to the predetermined desired phase value $\varphi_{N\_DES}$, respectively after a change of the resonant frequency $f_R$ as a result of a change of density $\rho$ of the medium guided in the at least one measuring tube 10, a corresponding changed frequency value can be quickly tuned in. As further evident from FIG. 8, the control value on the output of the frequency controller CTRL can, for example, already serve also as a frequency measured value $X_f$, respectively be supplied to a computing means CALC generating the density measured value $X_\rho$, for example, namely a computing means executing the above mentioned calculational specification (3) for ascertaining the density measured value $X_\rho$ and/or formed by means of a calculation routine executed by a microprocessor of the measuring device electronics. Instead of a phase locked loop, a further option is, of course, to use another frequency control circuit suitable for setting the wanted frequency $f_N$ and known, per se, to those skilled in the art, for example, also such, which operate based on a mutual coupling of the exciter signal $e_1$ to the at least one oscillation measurement signal $s_1$.

For correction of measuring principle related, almost unavoidable, really not directly disregardable dependencies of the wanted frequency on additional physical influencing variables, namely physical influencing variables other than density and viscosity, not least of all also a temperature of the medium, respectively a temperature distribution in the measuring transducer resulting therefrom and/or a, for example, elastic, respectively reversible, deformation of the at least one measuring tube, respectively a stress distribution in the measuring transducer resulting therefrom, respectively for compensating possible cross sensitivities of the measuring transducer to said influencing variables, the density measuring device of the invention can, in case required and such as quite usual in the case of density measuring device of the type being discussed, furthermore, comprise, thermally coupled with the at least one measuring tube 10, a temperature sensor, which—such as indicated in FIG. 3—is adapted to register a temperature of the at least one measuring tube and to transduce such into a temperature measurement signal $\theta 1$ representing such, and/or, mechanically coupled with the at least one measuring tube, a strain sensor, which—such as indicated in FIG. 3—is adapted to register a strain of the at least one measuring tube and to transduce such into a strain measurement signal ($\epsilon 1$) representing such. Equally, the measuring device electronics, for example, namely also its measuring- and evaluating circuit, can be adapted to ascertain, by means of the temperature measurement signal $\theta 1$, at least one temperature measured value $X_\Theta$, which represents a temperature of the at least one measuring tube, respectively by means of the strain measurement signal $\epsilon 1$, to a certain at least one strain measured value $X_\epsilon$, which represents a strain of the at least one measuring tube, respectively to a certain a mechanical stress within the at least one measuring tube resulting from the deformation of the measuring transducer, as well as to generate the density measured value $X_\rho$ with application also of the temperature measured value $X_\Theta$, respectively the strain measured value $X_\epsilon$.

Using the previously indicated dependence of the phase shift angle $\varphi_N$ and wanted frequency $f_N$ on density and viscosity, it is additionally also possible with the density measuring device of the invention, supplementally to density $\rho$, to a certain also the viscosity $\eta$ of the medium guided in the at least one measuring tube, for example, in that the measuring device electronics ascertains during the phase control interval based on the oscillation measurement signal $s_1$ and/or the exciter signal at least one damping measured value $X_D$, which represents a damping counteracting the wanted oscillations of the at least one measuring tube, and—such as, among other things, also provided in the above mentioned U.S. Pat. Nos. B 6,651,513 or B 6,006,609, generates, based on the damping measured value $X_D$, a viscosity measured value $X_\eta$ representing the viscosity $\eta$ of the medium. Alternatively or supplementally, the viscosity $\eta$ can also be ascertained in that, before and/or after the phase control interval, consequently, respectively after the wanted frequency $f_N$ firstly required for measuring the density $\rho$ has been set and based thereon the corresponding frequency measured value $X_f$ has first been ascertained, the measuring device electronics temporarily so sets the exciter signal $e_1$, consequently the mentioned drive force F, that the wanted force component and the velocity response then, such as already mentioned, respectively also shown in FIG. 6, fulfill the resonance condition ($\Re$), consequently the oscillation frequency of the actively excited oscillations correspond to the instantaneous resonant frequency $f_R$. On the basis thereof, the measuring device electronics can firstly ascertain an instantaneous frequency shift $\Delta f = f_N - f_R$, by which the wanted frequency $f_N$ set during the phase control interval $\Delta t_\varphi$ is greater in comparison to a reference resonant frequency, namely a resonant frequency of that natural mode of oscillation, whose (eigen-) oscillation form corresponds to the wanted oscillations, respectively a resonant frequency respectively nearest neighboring the wanted frequency $f_N$ set during the phase control interval, respectively the measuring device electronics can, at times, generate a frequency difference measured value $X_{\Delta f}$ instantaneously representing the frequency shift. The frequency shift $\Delta f$ is correlated with the bandwidth B, respectively with the quality factor Q, of the oscillatory mode excited with its instantaneous resonant frequency $f_R$, in such a manner that the frequency shift $\Delta f$ equally can serve such as the bandwidth ($B^2 \sim \eta$), respectively the quality factor ($Q^{-2} \sim \eta$), as a measure for the viscosity, consequently the viscosity measured value $X_\eta$ can be generated with application of the frequency difference measured value $X_{\Delta f}$, for example, based on the formula:

$$X_\eta = C + D \cdot \sqrt{X_{\Delta f}} \qquad (4)$$

Accordingly, the measuring device electronics according to an additional embodiment of the invention is adapted outside of the phase control interval $\Delta t_\varphi$, for example, directly therebefore and/or directly thereafter, to adjust the wanted force component, respectively its excitation frequency, at least temporarily in such a manner that the phase shift angle $\Delta \varphi_N$ amounts to not less than $-5°$ and no greater than $+5°$; this, especially also in such a manner that the phase shift angle $\Delta \varphi_N$ actually amounts to not less than $-2°$ and/or no greater than $+2°$, that namely the excitation frequency of the wanted force component, as well as also usual in the case of conventional density measuring devices, essentially corresponds to an instantaneous, resonant frequency of the at least one measuring tube, consequently the wanted oscillations of the at least one measuring tube are temporarily resonant oscillations outside of the phase control interval $\Delta t_\varphi$. With application of the resonant frequency—in the case of the density measuring device of the invention only useful as an additional wanted frequency-, among other things, the viscosity of the medium guided in the at least one measuring tube can be ascertained in the above-described manner. The wanted oscillations actively excited to resonant frequency, for example, during a starting up of the density measuring device and/or recurringly during operation, can, furthermore, also serve to adapt the measuring device electronics, with targeting, to the measuring point formed by means of the density measuring device in interaction with the connected pipeline and/or to change of the medium possibly occurring during operation, for example, in such a manner that the mentioned phase control desired value $\Phi_{N\_DES}$ is correspondingly finely adjusted, and/or in the course of a recurringly performed self-test to check the integrity, respectively the ability of the density measuring device to function, for example, in such a manner that a significant deviation diagnosed by means of the measuring device electronics of one or more resonance frequencies from fixed standard values leads to the issuance of a warning report signaling lessened ability to function and/or lessened accuracy of measurement. Moreover, the wanted oscillations excited to resonant frequency can also serve to a certain a starting value, from which the controlling of the phase shift angle $\Delta \varphi_N$ by the measuring device electronics can be begun, respectively from which, after a temporarily too high control error signal, for example, after an abrupt change of a resonant frequency of the measuring tube by greater than 1 Hz, for instance, as a result of a change in the medium, respectively in the case of temporarily significantly fluctuating density, for instance, as a result of inhomogeneities temporarily formed in the medium, such as gas bubbles, respectively solid particles, entrained in a liquid, the phase shift angle $\Delta \varphi_N$ can be rapidly brought back to the desired phase value $\Delta \varphi_{N\_DES}$.

For the operationally provided case, in which the medium to be measured flows through the at least one measuring tube, consequently the mass flow, respectively the mass flow rate ṁ, is different from zero, the measuring tube 10 at the same time vibrating in the above described manner, namely performing wanted oscillations with a wanted frequency differing from the instantaneous resonant frequency, induces in the medium flowing through, besides inertial, respectively friction, forces, additionally also Coriolis forces. These, in turn, react on the measuring tube 10 and so bring about additional oscillations of the same, registrable by sensor, and, indeed, essentially according to an additional natural oscillation form of a higher modal order in comparison with the oscillation form of the wanted oscillations, namely with a comparatively higher number of oscillation nodes, respectively oscillation antinodes. An instantaneous development of these so-called Coriolis oscillations superimposed on the excited wanted oscillations and of frequency equal thereto depends, in such case, especially as regards its amplitude, especially, also on the instantaneous mass flow rate.

Serving as Coriolis oscillations supplementally evaluated for the purpose of measuring the mass flow rate can in the case of a curved measuring tube be, for example, rotary oscillations executed by this then, supplementally to the bending oscillations serving as wanted oscillations, about an imaginary rotary oscillation axis directed perpendicular to the oscillation axis and imaginarily intersecting the center line of the at least one measuring tube 10 in the region of its half oscillatory length.

For measuring of the mass flow rate ṁ, respectively the total mass flow, the measuring transducer according to an additional embodiment of the invention includes, furthermore, a second oscillation sensor 52, for example, one equally-constructed to the first oscillation sensor 51. The second oscillation sensor 52 serves to register oscillatory movements of the at least one measuring tube and to transduce such into a second oscillation measurement signal s2 representing such and having a signal frequency corresponding to the wanted frequency. The oscillation sensor 52 can be embodied, same as the oscillation sensor 51, for example, as an electrodynamic oscillation sensor or, however, for example, also as a capacitively formed oscillation sensor. For the above described case, in which the inner part is formed by means of a measuring tube 10 and a counteroscillator 20 coupled with such, the oscillation sensors 51, 52, can in advantageous manner furthermore be so embodied and so placed in the measuring transducer that each of the oscillation sensors registers, for example, differentially, predominantly oscillations of the measuring tube 10 relative to the mentioned counteroscillator 20, that thus both the oscillation measurement signal Si as well as also the oscillation measurement signal $s_2$ represent oscillatory movements of the at least one measuring tube 10 relative to the mentioned counteroscillator 20.

Said oscillation sensor 52, as usual in the case of measuring transducers used in Coriolis mass flow-/density measuring devices, is arranged along the measuring tube 10, consequently spaced in the flow direction from the oscillation sensor 51 on the measuring tube 10, for example, in such a manner that, such as evident from FIG. 3, 4 or 5, respectively their combination, the oscillation sensor 51 on the inlet side and the oscillation sensor 52 on the outlet side are arranged, consequently adapted, to register oscillatory movements on the inlet side, respectively on the outlet side. In the example of an embodiment shown here, each of the oscillation sensors 51, 52 is additionally, such as quite usual in the case of measuring transducers of the type being discussed, equally spaced from the center of the at least one measuring tube 10, respectively from the oscillation exciter 41—here namely a single oscillation exciter placed at the half oscillatory length.

As a result of the Coriolis oscillations also executed by the measuring tube 10, its inlet side, oscillatory movements registered by the oscillation sensor 51 and its outlet side, oscillatory movements registered by the oscillation sensor 52 have phase positions differing from one another, in such a manner that, as a result, a travel-time difference $\Delta t$, respectively a corresponding phase difference $\Delta \varphi = 2\pi \cdot f_N \cdot \Delta t$, between the oscillation measurement signal s1 and the oscillation measurement signal s2 dependent on the mass flow rate ṁ of the medium flowing in the lumen of the at least one measuring tube 10 exists, consequently is measurable. As a result of this, with application both of the oscillation signal s1 delivered by the oscillation sensor 51 during the respective phase control interval $\Delta t_\varphi$ as well as also the oscillation signal s2 simultaneously delivered, respectively delivered during the phase control interval, by the oscillation sensor 52, the measuring device electronics can supplementally to density also ascertain the mass flow rate of the medium flowing through the measuring tube during the phase control interval. In an additional embodiment of the invention, the measuring device electronics is, consequently, furthermore, also adapted, during the phase control interval $\Delta t_\varphi$ and based on both the first oscillation measurement signal s1 as well as also the second oscillation measurement signal s2 supplementally to ascertain a phase difference measured value $X_{\Delta\varphi}$, which represents the phase difference $\Delta\varphi_m$ dependent on the mass flow rate $\dot{m}$ for the phase control interval $\Delta t_\varphi$; this, especially, in order thereafter to generate based on the phase difference measured value $X_{\Delta\varphi}$ a mass flow measured value $X_m$ representing the mass flow rate, respectively the total mass flow. Alternatively or supplementally, the measuring device electronics is adapted, furthermore, to adjust the wanted force component $F_N$, respectively the phase shift angle also by means of the second oscillation measurement signal s2, especially namely based on both the oscillation measurement signal s1 as well as also the oscillation measurement signal s2, for example, in such a manner that by means of the oscillation measurement signal s1 as well as the oscillation measurement signal s2 firstly a sensor sum signal representing the oscillatory movements of the measuring tube 10 at the site of the oscillation exciter, respectively the point of engagement, is formed therewith, respectively a sensor sum signal at least phase equal therewith, especially a digital sensor sum signal, is formed and thereafter the sum signal is fed as digital oscillation measurement signal $s_{1D}$ to the first input of the phase comparator COMP of the mentioned phase locked loop (PLL), consequently used for control of the phase locked loop. Moreover, additionally, also the frequency measured value $X_f$ can be ascertained with application of the oscillation signal s2, for example, also based on both the oscillation measurement signal s1 as well as also the oscillation measurement signal s2.

It is noted here that—although the measuring transducer in the representative example of an embodiment shown in FIGS. 4 and 5 has only a single curved measuring tube and at least, insofar, resembles in its mechanical construction, as well as also its principle of action, the measuring transducers proposed in the above the U.S. Pat. No. 7,360,451, respectively U.S. Pat. No. 6,666,098, respectively also those sold by the applicant under the type designations "PROMASS H", "PROMASS P" or "PROMASS S"—, of course, also other measuring transducers of the type discussed herein can serve for implementing the invention, not least of all also those with straight and/or more than one measuring tube, for instance, comparable to the measuring transducers shown in the above the U.S. Pat. Nos. A 6,006,609, B 6,513,393, B 7,017,424, B 6,840,109, 6,920,798, A 5,796,011, respectively U.S. Pat. No. B 7,549,319 or, for example, also those sold by the applicant under the type designations "PROMASS I", "PROMASS E", "PROMASS F" or "PROMASS X" (http://www.the.endress.com/#products/coriolis). In accordance therewith, the measuring transducer can also have a single straight measuring tube or at least two measuring tubes, for example, mechanically coupled with one another by means of an inlet side, flow divider and an outlet side, flow divider, in given cases, supplementally also by means of at least one, inlet side, coupling element and at least one, outlet side, coupling element, and/or constructed equally to one another and/or curved and/or mutually parallel measuring tubes for guiding medium to be measured, which during operation at least at times vibrate for producing the primary signals, for instance, with equal frequency at a shared oscillation frequency, however, with phases opposite one, or the measuring transducer can be formed, for example, also by means of four straight measuring tubes or by means of four curved measuring tubes.

The invention claimed is:

1. A density measuring device, for measuring density of a flowable medium, said measuring device comprising:

measuring device electronics; and a measuring transducer electrically connected with said measuring device electronics, said measuring transducer including:

at least one measuring tube;

an oscillation exciter, for exciting and maintaining oscillations, of said at least one measuring tube; and a first oscillation sensor, for registering oscillations of said least one measuring tube, wherein:

said at least one measuring tube exhibits a lumen surrounded by a tube wall and is adapted to guide medium in its lumen and during such guidance to be caused to vibrate in such a manner that said at least one measuring tube executes wanted oscillations, namely mechanical oscillations, about a resting position with a wanted frequency;

said first oscillation sensor, is adapted to register oscillatory movements of said at least one measuring tube and to transduce such into a first oscillation measurement signal representing such;

said measuring device electronics is adapted to transduce, by means of an exciter signal, supplied electrical power into a drive force acting on a point of engagement of said at least one measuring tube formed by means of said oscillation exciter;

said drive force includes a wanted force component introduced into said at least one measuring tube, namely a periodic force component changing with an excitation frequency corresponding to the wanted frequency and effecting the wanted oscillations;

said measuring device electronics is further adapted to adjust, by means of said first oscillation measurement signal as well as said exciter signal, said drive force, namely the wanted force component, respectively its excitation frequency, in such a manner that during a predetermined phase control interval, a phase shift angle, by which a velocity response of said at least one measuring tube, namely a velocity of the oscillatory movements of said at least one measuring tube at the point of engagement changing with the wanted frequency as a function of time, is phase shifted from said wanted force component of said drive force, amounts between 20° and 80°, wherein a dependence of the wanted frequency on the damping of the wanted oscillations is less than the dependence of the wanted frequency on the damping of the wanted oscillations at resonance.

2. The density measuring device as claimed in claim 1, wherein:

said first oscillation measurement signal includes a signal frequency corresponding to the wanted frequency.

3. The density measuring device as claimed in claim 1, wherein:

said exciter signal includes a signal frequency corresponding to the wanted frequency.

4. The density measuring device as claimed in claim 1, wherein:

said measuring device electronics is adapted to adjust the drive force, by changing a signal frequency of said exciter signal.

5. The density measuring device as claimed in claim 1, wherein:
said measuring device electronics is adapted to bring the phase shift angle, during the total phase control interval or for a duration of greater than 10 ms to a predetermined phase value.

6. The density measuring device as claimed in claim 5, wherein:
said measuring device electronics has a phase locked loop, for setting said phase shift angle.

7. The density measuring device as claimed in claim 1, wherein: said measuring device electronics is adapted to change a signal frequency of said exciter signal until the phase shift angle, has achieved a predetermined desired phase value.

8. The density measuring device as claimed in claim 1, wherein:
said measuring tube is adapted to be flowed through by the medium with a mass flow rate, during execution of the wanted oscillations.

9. The density measuring device as claimed in claim 1, wherein:
said measuring transducer has a second oscillation sensor spaced along said measuring tube from said first oscillation sensor, for registering oscillations, of said at least one measuring tube; and
said second oscillation sensor is adapted to register oscillatory movements of said at least one measuring tube and to transduce such into a second oscillation measurement signal representing such.

10. The density measuring device as claimed in claim 9, wherein:
said second oscillation measurement signal includes a signal frequency corresponding to the wanted frequency.

11. The density measuring device as claimed in claim 9, wherein:
said measuring device electronics is adapted to ascertain the frequency measured value, based on both said first oscillation measurement signal as well as also said second oscillation measurement signal or
said measuring device electronics is adapted to adjust the wanted force component also by means of the second oscillation measurement signal.

12. The density measuring device as claimed in claim 9, wherein:
said measuring tube is adapted to be flowed through by the medium with a mass flow rate, during execution of the wanted oscillations, in order to induce in the flowing medium Coriolis forces dependent on its mass flow rate, which Coriolis forces are suitable to bring about Coriolis oscillations superimposed on the wanted oscillations and of frequency equal thereto, in such a manner that between said first oscillation measurement signal and said second oscillation measurement signal a phase difference, exists dependent on the mass flow rate.

13. The density measuring device as claimed in claim 12, wherein:
said measuring device electronics is adapted based on both said first oscillation measurement signal as well as also said second oscillation measurement signal to generate a mass flow measured value, representing the mass flow rate.

14. The density measuring device as claimed in claim 12, wherein:
said measuring device electronics is adapted during the phase control interval based on both said first oscillation measurement signal as well as also said second oscillation measurement signal to ascertain a phase difference measured value, which represents the phase difference, dependent on the mass flow rate, for the phase control interval.

15. The density measuring device as claimed in claim 14, wherein:
said measuring device electronics is adapted to generate the mass flow measured value, based on the phase difference measured value.

16. The density measuring device as claimed in claim 1, wherein:
said measuring device electronics is adapted outside of the phase control interval to adjust the wanted force component, in such a manner that the phase shift angle, between −5° and +5°.

17. The density measuring device as claimed in claim 1, wherein:
said measuring device electronics is adapted outside of the phase control interval to adjust the wanted force component, at least temporarily, in such a manner that the wanted oscillations of said at least one measuring tube at times are resonant oscillations, consequently the wanted frequency corresponds at times to a resonant frequency of said at least one measuring tube.

18. The density measuring device as claimed in claim 1, wherein:
said measuring transducer is produced in micro system technology; or
said tube wall of said at least one measuring tube is composed of silicon; or
said at least one measuring tube, shows a caliber, which is less than 1 mm.

19. The density measuring device as claimed in claim 1, wherein:
said tube wall of said at least one measuring tube is composed of a metal, or
said at least one measuring tube shows a caliber, which is greater than 1 mm.

20. The density measuring device as claimed in claim 1, further comprising:
a temperature sensor thermally coupled with said at least one measuring tube, which is adapted to register a temperature of said at least one measuring tube and to transduce such into a temperature measurement signal representing such;
said measuring device electronics is adapted by means of the temperature measurement signal to ascertain at least one temperature measured value, which represents a temperature of said at least one measuring tube; and
said measuring device electronics is adapted to generate the density measured value, with application also of the temperature measured value.

21. The density measuring device as claimed in claim 1, further comprising:
a strain sensor mechanically coupled with said at least one measuring tube, which is adapted to register a strain of said at least one measuring tube and to transduce such into a strain measurement signal representing such;
said measuring device electronics is adapted, by means of said strain measurement signal, to ascertain at least one strain measured value, which represents a strain of said at least one measuring tube, respectively a mechanical stress within said at least one measuring tube; and said measuring device electronics is adapted to generate the density measured value with application also of the strain measured value.

22. The density measuring device as claimed in claim 1, wherein:
said measuring device electronics is adapted based on said first oscillation measurement signal or said exciter signal to generate a viscosity measured value, which represents the viscosity, of the medium.

23. The use of a density measuring device as claimed in claim 1, for measuring density of a medium, flowing in a pipeline.

24. The use of a density measuring device as claimed in claim 13, for measuring a mass flow rate of a medium flowing in a pipeline.

25. The use of a density measuring device as claimed in claim 24, for measuring viscosity of a medium flowing in a pipeline.

26. The density measuring device as claimed in claim 1, wherein: the predetermined phase control interval is not less than 10 ms.

27. The density measuring device as claimed in claim 1, wherein: said phase shift angle is constant during said phase control interval.

28. The density measuring device as claimed in claim 16, wherein: said measuring device electronics is adapted outside of the phase control interval to adjust the wanted force component, at least temporarily, in such a manner that the excitation frequency of the wanted force component corresponds to a resonant frequency of said at least one measuring tube.

\* \* \* \* \*